(12) United States Patent
Oshima et al.

(10) Patent No.: US 6,197,282 B1
(45) Date of Patent: Mar. 6, 2001

(54) FINE ULTRAVIOLET SCREENING PARTICLES, PROCESS FOR PREPARING THE SAME, AND COSMETIC PREPARATION

(75) Inventors: Kentaro Oshima; Shunji Kozaki; Yoshinobu Imaizumi; Toshio Miyake; Keiichi Tsuto, all of Wakayama; Kazuhiro Yamaki; Satoshi Sugawara, both of Tokyo, all of (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/194,199
(22) PCT Filed: May 27, 1997
(86) PCT No.: PCT/JP97/01788
  § 371 Date: Nov. 20, 1998
  § 102(e) Date: Nov. 20, 1998
(87) PCT Pub. No.: WO97/45097
  PCT Pub. Date: Dec. 4, 1997

(30) Foreign Application Priority Data

May 30, 1996 (JP) .................................................. 8-160541

(51) Int. Cl.$^7$ ............................ A61K 7/42; A61K 7/035; A61K 7/00
(52) U.S. Cl. ............................... 424/59; 424/69; 424/401
(58) Field of Search ................................ 424/401, 59, 69

(56) References Cited

U.S. PATENT DOCUMENTS 4,927,464 * 5/1990 Cowie ................................... 106/436
5,714,260 * 2/1998 Okuda et al. ......................... 428/402

* cited by examiner

*Primary Examiner*—Shelley A. Dodson
*Assistant Examiner*—Marina Lamm
(74) *Attorney, Agent, or Firm*—Birch, Stewart, Kolasch & Birch, LLP

(57) ABSTRACT

The present invention provides a method for producing a material dispersed with ultraviolet shielding fine particles, characterized by subjecting a starting material liquid mixture comprising particles comprising one or more inorganic substances having shielding abilities against ultraviolet light, one or more silicone dispersants selected from modified silicones and reactive silicones, and a silicone oil to a mill treatment and/or a high-pressure dispersion treatment; and ultraviolet shielding fine particles or a material dispersed therewith, characterized by being produced by the above method. Also, the present invention provides a method of producing a powdery product of ultraviolet shielding fine particles, characterized by drying the material dispersed with ultraviolet shielding fine particles obtainable by the above method. Further, the present invention provides cosmetics comprising a material dispersed with ultraviolet shielding fine particles or a powdery product of the ultraviolet shielding fine particles. The material dispersed with ultraviolet shielding fine particles of the present invention is characterized in that the ultraviolet shielding fine particles comprise particles comprising one or more inorganic substances having shielding abilities against ultraviolet light, surfaces thereof being coated with one or more silicone dispersants selected from modified silicones and reactive silicones, and that at least a part of the ultraviolet shielding fine particles is dispersed in a silicone oil as aggregated particles of the particles comprising inorganic substances.

17 Claims, 9 Drawing Sheets

FINE ULTRAVIOLET SCREENING PARTICLES, PROCESS FOR PREPARING THE SAME, AND COSMETIC PREPARATION

This application is the national phase under 35 U.S.C. §371 of prior PCT International Application No. PCT/JP97/01788 which has an International filing date of May 27, 1997 which designated the United States of America.

TECHNICAL FIELD

The present invention relates to ultraviolet shielding fine particles having substantially no catalytic activities and high shielding abilities in the ultraviolet light region, a method for producing the same, and cosmetics.

BACKGROUND ART

Of the sunlight reaching the earth (including infrared light, visible light, and ultraviolet light), 5 to 6% is ultraviolet light. The ultraviolet light has short wavelengths, and thus comprises high-energy electromagnetic waves. Therefore, the ultraviolet light has been widely known to have degradability against many kinds of substances, thereby causing damages to living bodies.

Therefore, ultraviolet shielding agents have been used for applications of protecting skin from causing inflammation or skin cancer due to the ultraviolet light by formulating them in cosmetics, or preventing a pigment from discoloration due to decomposition by ultraviolet light by mixing them in paints. By such applications, an unnatural whitening in cases of the cosmetics or a loss of coloration in cases of the paints can be prevented by increasing the transparency in the visible light region. Therefore, it is desired that the ultraviolet light is protected while the transparency in the visible light region is maintained.

The ultraviolet shielding agent comprising organic compounds as effective ingredients prevents the transmission of the ultraviolet light on account of the specific absorption of the composition against the ultraviolet light. For example, an ultraviolet absorbable composition comprising substituted N,N'-bis-aromatic formamidines, and the like are known (Japanese Patent Examined Publication No. 61-09993). However, while absorbing the ultraviolet light, the organic ultraviolet shielding agents have the problem of degradation on accounts of the absorption, with the result of an undesirable lowering of the shielding abilities with the passage of time. In their applications to cosmetics, the kinds and amounts of the ultraviolet shielding agents formulated are restricted owing to effects caused on human bodies, and thus it is difficult to achieve a good shielding performance within a controlled range.

On the other hand, in the ultraviolet shielding agent using an inorganic compound, the composition is formulated with inorganic fine particles, and the transmission of the ultraviolet light is prevented by the absorbing ability and the scattering ability against the ultraviolet light owned by the composition. In the inorganic ultraviolet shielding agent, the composition is not degraded with the passage of time and causes little damages on the human bodies, so that it is superior to the organic ultraviolet shielding agent. However, when compared with organic ultraviolet shielding agents, since the inorganic ultraviolet shielding agents are in the form of particles, it has been conventionally considered to be rather difficult to protect against the ultraviolet light with inorganic ultraviolet shielding agents while maintaining high transparency in the visible light region.

In order to effectively exhibit the shielding abilities in the ultraviolet light region while maintaining high transparency in the visible light region (light wavelengths of from 400 to 800 nm), the composition has to be made ultrafine to be in a state of high dispersion to thereby increase the shielding abilities against the ultraviolet light. However, in the case of using such ultrafine particles, problems may arise in the dispersion stability due to the aggregation ability of the ultrafine particles, and in the catalytic activities of the ultrafine particles.

In order to improve dispersibility, there have been known methods of improving surfaces of the ultrafine particles by coating with other substances, including, for instance, an invention concerned with cosmetics formulating powdery products of zinc oxide fine particles coated with an anionic surfactant (Japanese Patent Examined Publication No. 5-77644); an invention concerned with a method of producing powdery products of zinc oxide ultrafine particles coated with an anionic surfactant (Japanese Patent Laid-Open No. 62-260716), and the like. In the above publications, the method comprises the steps of surface-treating the particles in an aqueous solution, solvent-replacing with an organic solvent, and drying, in which the number of the production steps is large, and also process is complicated. Also, in publications other than those mentioned above, there have been known, for instance, an invention concerned with a composition for cosmetics comprising metal oxide fine particles coated with a surfactant and a method of producing the same (Japanese Patent Laid-Open No. 62-84017). In this publication, the method comprises the steps of surface-treating the particles in a liquid phase, aggregating and filtering, washing, dehydrating, and blending, in which the number of the production steps is extremely large as in the method mentioned above, and the process is very complicated.

In publications other than those mentioned above, there have been known, for instance, an invention concerned with a method of producing zinc oxide fine particles obtainable by heating a mixture comprising zinc or a zinc compound, a carboxyl group-containing compound, and an alcohol (Japanese Patent Laid-Open No. 7-232919); an invention concerned with composite oxides for shielding against ultraviolet light obtainable by the steps of reacting an acidic solution containing at least one member selected from zinc, lanthanum, cerium are the like with an alkali solution, filtering, washing, drying, firing, and subsequently surface-treating with a silicone oil or a fatty acid, and a method of producing the same (Japanese Patent Laid-Open No. 5-222317), and the like. In these publications, the reaction step is an essential step in the production processes, which is noted to accompanied the complication of controlling the reaction.

In publications other than those mentioned above, there have been known an invention concerned with cosmetics characterized by containing a powder obtainable by subjecting titanium oxide to a coating treatment with mixed hydrates comprising particular amounts of silicate hydrates and alumina hydrates, wherein the titanium oxide is nearly spherical or irregularly shaped and has an average particle size of from 30 to 70 nm, and further subjecting the surfaces to a coating treatment with a silicone oil (Japanese Patent Laid-Open No. 2-247109). However, the process of coating treatment with mixed hydrates comprising the silicate hydrates and the alumina hydrates before the particle surface is subjected to a surface treatment with a silicone oil is required, which is noted to be accompanied with the complication in the reaction control of the mixed hydrates.

Next, for the purpose of providing a material dispersed with fine particles as to be used as water-repellant, ultraviolet shielding agents for sunscreen cosmetics, there have been known, for instance, an invention concerned with an oily, dispersed material obtainable by the step of pulverizing a mixture containing an oil, titanium dioxide particles, and an organic dispersant in the presence of a granular pulverizing medium, and a method of producing the same (Japanese Patent Examined Publication No. 6-61457); an invention concerned with a method of producing sunscreen obtainable by the step of pulverizing a mixture containing an oil, zinc oxide, titanium dioxide, and an organic dispersant in the presence of a granular pulverizing medium (Japanese Patent Laid-Open No. 5-201844); an invention concerned with a material dispersed with zinc oxide fine particles obtainable by the step of pulverizing a mixture containing an oil, zinc oxide particles, and an organic dispersant in the presence of a granular pulverizing medium (Japanese Patent Laid-Open No. 5-213618), and the like. In these publications, since the particle concentration in the dispersed material is as high as not less than 30%, its production is difficult, and the stability of the dispersed material is low. In addition, a silicone oil which is suitable to be formulated in sunscreen cosmetics as a dispersion medium from the aspects of good skin texture and good stability when used as cosmetics is not used, nor a dispersant suitable for the silicone oil is used. Therefore, there is a limitation of the amount of these dispersed materials formulated in sunscreen cosmetics, so that the dispersibility of the particles and the stability of the dispersed material are poor.

Also, there have been known an invention concerned with a dispersed liquid of titanium dioxide obtainable by the step of pulverizing a mixture containing titanium dioxide and an organic compound having a suitable branched chain in the absence of a dispersing aid, a cosmetic composition thereof, and a method of using the same (Japanese Patent Unexamined Publication No. 8-507081). In this publication, since an organic compound having a branched chain acting as a dispersant is used as a dispersion medium, the amount formulated in cosmetics is limited.

In publications other than those mentioned above, there have been known, for instance, an invention concerned with cosmetics formulated with inorganic powdery products of fine particles surface-treated with an organic silicon compound by a wet pulverization or a wet disintegration using a medium agitation mill (Japanese Patent Laid-Open No. 8-104606); an invention concerned with an oily, dispersed material comprising titanium oxide fine particles surface-improved with a particular alkylalkoxysilane dispersed in a water-repellent solvent or oily agent (Japanese Patent Laid-Open No. 8-119832); an invention concerned with cosmetics comprising metal oxide ultrafine particles having a particle size of not more than 0.1 μm, a dispersion medium, and a dispersant, the ultrafine particles having a particle size of the dispersed particles of not more than 0.1 μm, the content of the fine particles being not less than 10% by weight (Japanese Patent Laid-Open No. 6-239728), and the like. In these publications, since siloxanes and silanes are used as dispersants, the firing step is required.

Further, in publications other than those mentioned above, there has been known an invention concerned with a colloidal zinc oxide obtainable by the steps of heating zinc carbonate to form zinc oxide agglomerates, adding the agglomerates in a polyacrylic acid dispersed liquid, and pulverizing them (Japanese Patent Unexamined Publication No. 8-510440). In this publication, the method requires a reaction process, which would be noted to have complications in reaction control.

Also, for the purpose of providing a material dispersed with aqueous ultrafine particles, the ultrafine particles being stably dispersed to be used as hydrophilic ultraviolet shielding agents used in such applications as sunscreen cosmetics, there have been proposed, for instance, an invention concerned with a dispersed material obtainable by pulverizing a mixture of water, acicular titanium dioxide and a polycarboxylic acid or a salt thereof used as a dispersant in the presence of a granular pulverizing medium (Japanese Patent Laid-Open No. 2-212315); an invention concerned with an aqueous dispersed material containing water as a dispersion medium, titanium oxide ultrafine particles and a nonionic surfactant, the material dispersed with titanium dioxide of which particle surfaces of the titanium oxide ultrafine particles are subjected to a hydrophobic treatment (Japanese Patent Laid-Open No. 7-247119), and the like. The material dispersed with the fine particles in the above publication is an aqueous dispersed material.

In order to solve the various problems in the ultraviolet shielding agents using the metal oxide fine particles mentioned above, in an invention concerned with ultraviolet shielding composite fine particles, a method for producing the same, and cosmetics (International Unexamined Publication No. WO95/09895, Japanese Patent Laid-Open No. 8-12961), an ultraviolet shielding agent having high transparency in the visible light and high shielding abilities against the ultraviolet light is developed by forming composites comprising the fine particles having shielding abilities (daughter particles) against the ultraviolet light and aggregates of fine particles (matrix particles) in which the daughter particles are dispersed, and by determining the combination thereof based on the heights of the band gap energies of the daughter particles and the matrix particles, so that it is made possible to optimize the optical properties owned by the ultrafine particles. This ultraviolet shielding agent is characterized by the following. The refractive index can be controlled in a wide range by changing the materials and proportions of the matrix/daughter particles, so that high transparency can be exhibited regardless of the shapes, the high transparency being exhibited even when dispersed in various media. The handleablity (transportation, surface treatment, blending, and the like) is made easy owing to the sizes of the order of the fine particles. The coloration is not impaired, thereby making it usable for cosmetics. However, when using this ultraviolet shielding agent for cosmetics, the amount of the ultraviolet shielding agent formulated has to be made large in cases where the shielding abilities against the ultraviolet light are to be made large. In such cases, the texture of the powdery product of the composite fine particles becomes too stiff, so that an upper limit of the formulated amount must be set so as not to impair the texture of the cosmetics. Also, when used for cosmetics, it is necessary to inhibit the catalytic activities owned by the ultrafine particles located near the surfaces of the composite fine particles. Also in publications other than those mentioned above, there have been known an invention concerned with solid, porous silica beads containing metal compounds, a method of producing the same, and powdery deodorant (Japanese Patent Laid-Open No. 4-65312); an invention concerned with zinc oxide-polymer composite fine particles, a method for producing the same, and use therefor (Japanese Patent Laid-Open No. 8-60022); an invention concerned with zinc oxide fine particles formed by composites comprising crystalline co-precipitates of zinc and a particular metal element added thereto, and use therefor (Japanese Patent Laid-Open No. 8-253317), and the like. In the above publications, as in the above cases, by using these composite fine particles for cosmetics, the amount of the composite fine particles formulated has to be made large in cases where the shielding abilities against the ultraviolet light have to be made large. In such cases, the texture of the powdery product of the composite fine particles becomes too stiff, so that an upper limit of the formulated amount must be set so as not to impair the texture of the cosmetics. Also, when used for cosmetics, it is necessary to inhibit the catalytic activities owned by the ultrafine particles located near the surfaces of the composite fine particles.

Therefore, in order to solve the problem of posing limitations in the shielding abilities against the ultraviolet light owing to the upper limit in the formulation mentioned above and the problem of inhibiting the catalytic activities of the composite fine particles, in an invention concerned with ultraviolet shielding composite fine particles, method for producing the same, and cosmetics (Japanese Patent Laid-Open No. 9-100112), further adding the features of remarkably increasing the degree of freedom of formulation by making an average particle size of the composite fine particles small and reducing the powdery texture to thereby increase the upper limit of formulation, and of substantially inhibiting the catalytic activities of the composite fine particles by coating the surface of the composite fine particles with an inorganic substance having substantially no catalytic activities to the designed concept of the ultraviolet shielding composite fine particles mentioned above (International Unexamined Publication No. WO95/09895 and Japanese Patent Laid-Open No. 8-12961), to solve the above problems. However, in the publication (Japanese Patent Laid-Open No. 9-100112), in the method for producing the ultraviolet shielding fine particles, after the particles are surface-treated, the steps of solvent-replacing and dispersing in the oily agent is required, which involves a large number of production steps, thereby making the method complicated.

DISCLOSURE OF THE INVENTION

The present invention is to solve the various problems in the ultraviolet shielding agents described above.

Specifically, an object of the present invention is to provide ultraviolet shielding fine particles with substantially inhibited catalytic activities, uniform and stable dispersion in the medium (for instance, cosmetics, paints, and the like), high shielding abilities in the ultraviolet light region, and good handleability.

Another object of the present invention is to provide a method for producing the ultraviolet shielding fine particles in a simple manner.

A still another object of the present invention is to provide cosmetics comprising the ultraviolet shielding fine particles, the cosmetics having good texture against skin and high stability of the shielding abilities against the ultraviolet light.

In connection with the particles comprising one or more inorganic substances having shielding abilities against the ultraviolet light, the present inventors have proposed ultraviolet shielding fine particles, surfaces of the particles are coated with a modified silicone dispersant and/or a reactive silicone dispersant in a silicone oil. In particular, by noting on the combinations of the particles comprising inorganic substances having the shielding abilities against the ultraviolet light, the dispersants, and the kinds of the dispersion media, they have found that the effects of the particles comprising inorganic substances having the shielding abilities against the ultraviolet light can be optimally exhibited while maintaining a state of high dispersion. In other words, by coating the particles comprising inorganic substances having the shielding abilities against the ultraviolet light in a silicone oil by using a modified silicone dispersant and/or a reactive silicone dispersant which have good adsorption to the particles comprising inorganic substances and high dispersibility in the silicone oil, they have found that the effects of the particles comprising inorganic substances having the shielding abilities against the ultraviolet light can be optimally exhibited while stably maintaining a state of high dispersion.

Further, the present inventors have found that in order to inhibit the catalytic activities of the particles comprising inorganic substances having the shielding abilities against the ultraviolet light, the surfaces of the above particles are coated with a modified silicone dispersant and/or a reactive silicone dispersant in a silicone oil, thereby making it possible to substantially inhibit the catalytic activities of the particles comprising inorganic substances. Therefore, since the surfaces of the particles comprising inorganic substances are coated with a modified silicone dispersant and/or a reactive silicone dispersant, the silicone oil or other dispersion media surrounding the particles are not liable to undergo deterioration by the catalytic activities or photocatalytic activities of the particles comprising inorganic substances having the shielding abilities against the ultraviolet light.

Further, the present inventors have found that since a starting material liquid mixture containing particles comprising inorganic substances having the shielding abilities against the ultraviolet light, the particles being in a state of primary particles of one or more kinds, and in a state of aggregated particles comprising aggregates of the primary particles, a modified silicone dispersant and/or a reactive silicone dispersant, and a silicone oil is subjected to a mill treatment and/or a high-pressure dispersion treatment, the surfaces of the particles comprising inorganic substances can be coated with the modified silicone dispersant and/or the reactive silicone dispersant and at the same time the particles comprising inorganic substances are subjected to pulverization or disintegration, so that the particles comprising inorganic substances can be well dispersed in the state of the primary particles and in the state of the aggregated particles comprising the aggregates of the primary particles by a simple method. By this method, they have found that it is possible to obtain a material dispersed with the ultraviolet shielding fine particles, and a powdery product of the ultraviolet shielding fine particles by drying the dispersed material, and that it is possible to obtain a material dispersed with the ultraviolet shielding fine particles and a powdery product of the ultraviolet shielding fine particles with good handleability. Also, it has been found by observation using a transmission electron microscope that the particles comprising inorganic substances in the silicone oil obtained by this method have such a structure that the primary particles and the aggregated particles are present in a mixed state as mentioned above. In the present invention, since the silicone oil can be incorporated into the aggregated particles, the refractive index of the aggregated particles of the particles comprising inorganic substances approximates to the refractive index of the silicone oil, so that the effects of improving transparency can be obtained. Further, in this method, by changing the kinds and amounts of the dispersants and addition methods thereof or by changing the conditions for mill treatment and/or high-pressure dispersion treatment, the particle size of the dispersed particles can be controlled, so that the skin texture is improved in a very fine particle size region. In the present specification, the term "particle size of dispersed particles" means the particle size of the dispersed particles of the ultraviolet shielding fine particles, and more concretely it means a primary particle size of the particles comprising inorganic substances or a particle size of the aggregated particles dispersed in a silicone oil.

Further, the present inventors have found that by adding a polar solvent having a good compatibility with the silicone oil in the process of the preparation of the starting material liquid mixture, and/or during or after the mill treatment and/or high-pressure dispersion treatment, coating with the dispersant to the particles comprising inorganic substances can be more easily carried out.

Therefore, since the ultraviolet shielding fine particles of the present invention comprise particles comprising one or more inorganic substances having shielding abilities against the ultraviolet light, wherein the particles have such a structure that the surfaces of the above particles are coated with a modified silicone dispersant and/or a reactive silicone dispersant, it is now made possible to solve the points to be improved in the above-mentioned invention concerned with ultraviolet shielding composite fine particles, a method for producing the same, and cosmetics (Japanese Patent Laid-Open No. 9-100112). In other words, the points to be improved are as follows. The proportion of the daughter particles in the composite fine particles is decreased owing to the coating of the particles by inorganic substances having substantially no catalytic activities, so that the shielding abilities against the ultraviolet light are decreased per unit weight of the composite fine particles including the surface coating corresponding to the above decrease. On the other hand, since the ultraviolet shielding fine particles of the present invention are not subjected to surface coating by inorganic substances, the shielding abilities against the ultraviolet light per unit weight of the fine particles consequently increase, thereby making it possible to solve the points.

Specifically, in sum, the present invention is concerned with the following:

(1) a method for producing a material dispersed with ultraviolet shielding fine particles, characterized by subjecting a starting material liquid mixture comprising particles comprising one or more inorganic substances having shielding abilities against the ultraviolet light, one or more silicone dispersants selected from modified silicones and reactive silicones, and a silicone oil to a mill treatment and/or a high-pressure dispersion treatment;

(2) the method for producing a material dispersed with ultraviolet shielding fine particles described in item (1), characterized in that the ultraviolet shielding fine particles substantially have no catalytic activities;

(3) the method for producing a material dispersed with ultraviolet shielding fine particles described in item (1) or (2), characterized in that the ultraviolet shielding fine particles have an average particle size of dispersed particles of from 0.01 to 5.0 $\mu$m;

(4) the method for producing a material dispersed with ultraviolet shielding fine particles described in any one of items (1) to (3), characterized in that the ultraviolet shielding fine particles are contained in an amount of from 0.1 to 40% by weight;

(5) the method for producing a material dispersed with ultraviolet shielding fine particles described in any one of items (1) to (4), wherein the particles comprising inorganic substances having shielding abilities against the ultraviolet light are one or more members selected from the group consisting of $TiO_2$, ZnO, $CeO_2$, $BaTiO_3$, $CaTiO_3$, $SrTiO_3$, and SiC;

(6) the method for producing a material dispersed with ultraviolet shielding fine particles described in any one of items (1) to (4), wherein the particles comprising inorganic substances having shielding abilities against the ultraviolet light comprise $TiO_2$ particles and ZnO particles;

(7) the method for producing a material dispersed with ultraviolet shielding fine particles described in any one of items (1) to (6), wherein the silicone dispersant is one or more silicone compounds selected from oxazoline-modified silicones, amino-modified silicones, and polyether-modified silicones;

(8) the method for producing a material dispersed with ultraviolet shielding fine particles described in any one of items (1) to (7), characterized in that a polar solvent having good compatibility with the silicone oil is further added in a process of the preparation of the starting material liquid mixture, and/or during or after the mill treatment and/or high-pressure dispersion treatment;

(9) ultraviolet shielding fine particles or a material dispersed therewith, characterized by being produced by the method of any one of items (1) to (8);

(10) a method of producing a powdery product of ultraviolet shielding fine particles, characterized by drying the material dispersed with ultraviolet shielding fine particles obtainable by the method of any one of items (1) to (8);

(11) a powdery product of ultraviolet shielding fine particles characterized by being produced by the method of item (10);

(12) cosmetics comprising the material dispersed with ultraviolet shielding fine particles of item (9);

(13) cosmetics comprising the powdery product of ultraviolet shielding fine particles of item (11);

(14) a material dispersed with ultraviolet shielding fine particles, characterized in that the ultraviolet shielding fine particles comprise particles comprising one or more inorganic substances having shielding abilities against the ultraviolet light, surfaces thereof being coated with one or more silicone dispersants selected from modified silicones and reactive silicones, and that at least a part of the ultraviolet shielding fine particles is dispersed in a silicone oil as aggregated particles of the particles comprising inorganic substances;

(15) the material dispersed with ultraviolet shielding fine particles described in item (14), characterized in that the ultraviolet shielding fine particles are contained in an amount of from 0.1 to 40% by weight; and

(16) the material dispersed with ultraviolet shielding fine particles described in item (14) or (15), characterized in that the ultraviolet shielding fine particles have an average particle size of dispersed particles of from 0.01 to 5.0 $\mu$m.

BEST MODE FOR CARRYING OUT THE INVENTION

Figure 1:
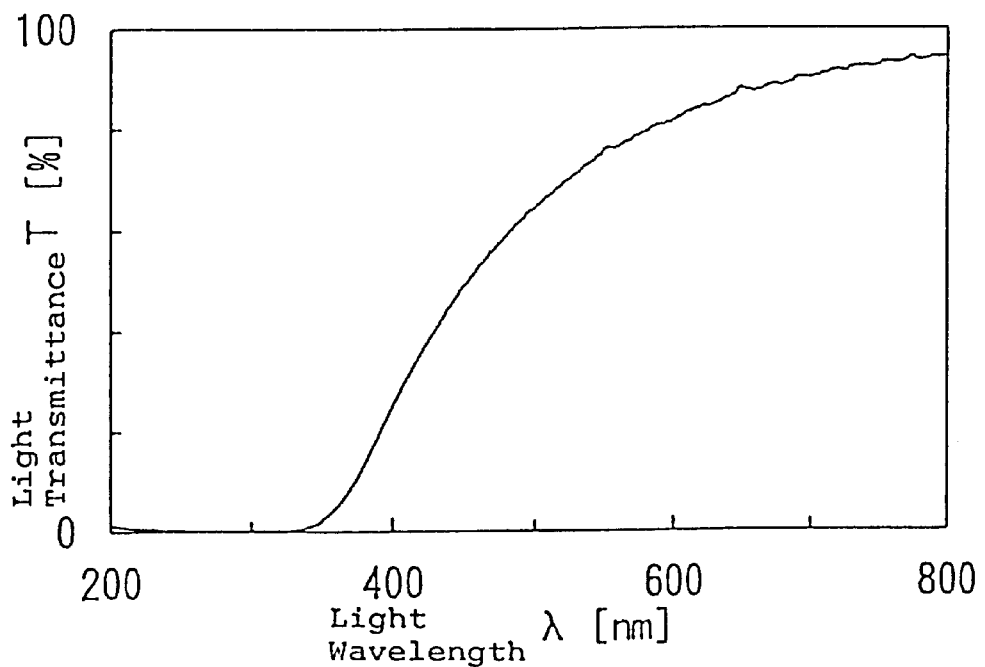
FIG. 1 is a chart showing the measurement results of the light transmittance of the material dispersed with ultraviolet shielding fine particles obtained in Example 1, as measured by an ultraviolet-visible light spectrophotometer.

The present invention will be explained in detail hereinbelow.

Particles comprising inorganic substances having a relatively small particle size and having high shielding abilities against ultraviolet light are likely to be aggregated, so that it is difficult to disperse them in a medium to exhibit their functions well. Therefore, in the present invention, the particles comprising inorganic substances, used in combination with a silicone dispersant and a silicone oil, are subjected to a mill treatment and/or a high-pressure dispersion treatment, so that the particles comprising inorganic substances can be maintained in a state of high dispersion in the silicone oil while coating the surfaces of the particles with the dispersant, thereby making it possible to maintain high transparency in the visible light and high shielding abilities against the ultraviolet light. Further, since the surfaces of the particles are coated by a dispersant, the catalytic activities of the particles comprising inorganic substances can be substantially inhibited. Further, while coating the surfaces of the particles with the silicone dispersant in the silicone oil, the material dispersed with the ultraviolet shielding fine particles can be obtained in a state of high dispersion, or a powdery product of the ultraviolet shielding fine particles can be obtained by drying the above material dispersed with the ultraviolet shielding fine particles. Therefore, the ultraviolet shielding fine particles having good handleability can be obtained.

In the present specification, the term "ultraviolet shielding fine particles" means primary particles of the particles comprising inorganic substances having shielding abilities against the ultraviolet light and aggregated particles formed by aggregates of these primary particles, and the term "material dispersed with the ultraviolet shielding fine particles" means a dispersed liquid comprising primary particles of the particles comprising inorganic substances having shielding abilities against the ultraviolet light, which constitute the ultraviolet shielding fine particles, and aggregated particles formed by aggregates of these primary particles dispersed in a silicone oil.

1. Starting Materials Used for Production of Ultraviolet Shielding Fine Particles First, each of the starting materials used for production methods of the present invention will be explained below.

(1) Particles Comprising Inorganic Substances Having Shielding Abilities Against Ultraviolet Light Constituting Ultraviolet Shielding Fine Particles The particles comprising inorganic substances constituting the ultraviolet shielding fine particles in the present invention have shielding abilities against the ultraviolet light. Further, it is preferred that the particles comprising inorganic substances have sizes of the level in which no absorption of the light in the visible light region takes place while no scattering of the visible light takes place.

In order to satisfy the requirements of having absorption of the ultraviolet light but preferably having no absorption in the visible light region, the inorganic substances constituting the ultraviolet shielding fine particles preferably have a wavelength for an exciton absorption of a band gap energy corresponding to the wavelengths in the ultraviolet light region. Specifically, semiconductive compounds having a band gap energy of from 2.7 to 4.0 eV are preferred. For instance, $TiO_2$, ZnO, $CeO_2$, $BaTiO_3$, $CaTiO_3$, $SrTiO_3$, SiC, and the like characteristically exhibit the above property, and one or more members selected from the group consisting of these compounds are preferred. Also, among them, $TiO_2$, ZnO, and $CeO_2$ are generally well used as ultraviolet shielding agents, and one or more members selected from the group consisting of these compounds are particularly preferred. In particular, in order to shield the light up to the ultraviolet light region A (320 to 400 nm), ZnO and $CeO_2$ are effectively used. Also, in order to shield the light of the ultraviolet light region B (280 to 320 nm), $TiO_2$ is effectively used. Incidentally, in order to shield both the light of the ultraviolet light region B and that of the ultraviolet light region A, it is preferred that the particles comprise $TiO_2$ and particles comprising one or more inorganic substances selected from the group consisting of ZnO, $CeO_2$, $BaTiO_3$, $CaTiO_3$, $SrTiO_3$, and SiC which are used in combination. In particular, it is preferred that $TiO_2$ and ZnO are used in combination.

Alternatively, in the case where $TiO_2$ is used, the shielding region can be extended to the ultraviolet light region A by incorporating, as impurity dopes, an element having a valence number of 5 or more, such as W, P, Ta, Nb, Sb, or Mo, or an element having a valence number of 3 or less, such as Zn, Al, Mg, or Ca.

The shapes of the particles comprising inorganic substances having shielding abilities against the ultraviolet light are not particularly limited, which may be spherical, plate-like or acicular. As for the scattering ability of the ultraviolet light, which is intensely exhibited by Mie scattering, in order to satisfy both transparency in the visible light region and shielding ability in the ultraviolet light region, the average particle size of the primary particles comprising inorganic substances is preferably from 0.001 to 1.0 μm. It is more preferred that the average particle size is from 0.001 to 0.7 μm, still more preferably from 0.001 to 0.5 μm, and particularly from 0.005 to 0.5 μm. Incidentally, the average particle size may be measured by a direct observation method (based on number) using an electron microscope.

In the present invention, since it is desired that the particles comprising inorganic substances having shielding abilities against the ultraviolet light are present in an easily dispersible state in the material dispersed therewith, the surfaces of the particles comprising inorganic substances may be coated with other substances, or they may be coated with silicones, or the particles comprising inorganic substances may be blended with a sol for dispersing aids, such as an $Al_2O_3$ sol, or with a sol stabilizer. For instance, in the case where $TiO_2$ ultrafine particles are used as the particles comprising inorganic substances, the surfaces of the ultrafine particles may be coated with oxides or hydrates of one or more elements selected from Al, Si, Zr, Mg, Zn, Ce, Ti, and Fe to improve dispersibility. Alternatively, the surfaces of the ultrafine particles may be treated with the silicones, or the ultrafine particles may be blended with a basic stabilizer, such as NH$_3$, to stabilize the state of the TiO$_2$ sol. Also, in the case where the ultrafine particle powder is surface-improved to achieve good dispersion, they can be used as the starting materials. The sol used in the present invention refers to fluids containing particles which cannot be generally observed by an ordinary optical microscope but having a particle size larger than that of an atom or that of a low molecular compound (see Iwanami Dictionary of Physics and Chemistry, Third Edition, published by Iwanami Publishers). Examples of sols include hydrosols of alumina, suspensions of TiO$_2$ ultrafine particles, and the like.

(2) Silicone Dispersant for Coating Surfaces of Particles

The silicone dispersants for coating surfaces of the particles include one or more silicone compounds selected from modified silicones and reactive silicones.

The modified silicones include polyether-modified silicones, alkyl-aralkyl-modified silicones, alkyl-aralkyl-polyether-modified silicones, alkyl-higher alcohol-modified silicones, alcohol-modified silicones, fluoro-modified silicones, long-chained alkyl-modified silicones, fluoroalkyl-modified silicones, alkylene oxide-modified silicones, alkylene oxide-modified silicone copolymers, silphenylene-modified silicone copolymers, ethylene-modified silicone copolymers, α-methylstyrene-modified silicone copolymers, carborane-modified silicone copolymers, bisphenol A carbonate-modified silicone copolymers, alkoxysilane-modified silicone copolymers, and other modified silicones.

The reactive silicones include oxazoline-modified silicones, amino-modified silicones, amino-polyether-modified silicones, epoxy-modified silicones, epoxy-polyether-modified silicones, carboxyl-modified silicones, carboxyl-polyether-modified silicones, carbinol-modified silicones, mercapto-modified silicones, phenol-modified silicones, vinyl-modified silicones, hydroxy-modified silicones, and other reactive silicones.

Among the silicones mentioned above, examples of those which can be relatively easily coated include the oxazoline-modified silicones, the amino-modified silicones, and the polyether-modified silicones. In particular, examples of those which can be more easily coated include the oxazoline-modified silicones and the amino-modified silicones. Here, as for the coating treatments using dispersants in the present invention, in principle, both chemical adsorption utilizing, for example, the electrostatic forces between the surfaces of the particles and the dispersant, and physical adsorption utilizing, for example, seed condensation of the dispersant using the particles as seeds can be employed.

(3) Dispersion Media

As for the dispersion media of the ultraviolet shielding fine particles surface-coated with a silicone dispersant, silicone oils may be used because the silicone dispersant exhibits high dispersibility in the dispersion medium. The silicone oils may be volatile or non-volatile silicone oils. Examples thereof include octamethyl polysiloxane, tetradecamethyl polysiloxane, methyl polysiloxane, high-polymerized methyl polysiloxane, methylphenyl polysiloxane, octamethyl cyclotetrasiloxane, decamethyl cyclopentasiloxane, and the like, and trimethylsiloxysilicate, and organopolysiloxanes having a repeating unit represented by the general formula (1) or the general formula (2) given below:

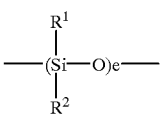

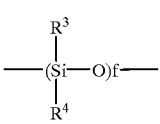

(wherein R$^1$ and R$^2$ each stands for an alkyl group having 1 to 4 carbon atoms; R$^3$ stands for an alkyl group, an alkenyl group, or a fluoroalkyl group, each being linear, branched, or cyclic, and having 1 to 40 carbon atoms; R$^4$ stands for an alkyl group, an alkenyl group, or a fluoroalkyl group, each being linear, branched, or cyclic, and having 7 to 40 carbon atoms; "e" stands for a number of not less than 2, and "f" stands for a number of not less than 3, wherein the sum of "e" and "f" is a number of 5 to 6,000.) Among these silicone oils, octamethyl cyclotetrasiloxane and decamethyl cyclopentasiloxane are preferably used. Incidentally, the silicone oils exemplified above may be used as a mixture.

The preferred combinations of the particles comprising inorganic substances having shielding abilities against the ultraviolet light, the silicone dispersant, and the dispersion medium may be the combinations where the particles comprising inorganic substances having shielding abilities against the ultraviolet light are TiO$_2$ and/or ZnO; the silicone dispersants are one or more members selected from oxazoline-modified silicones, amino-modified silicones, and polyether-modified silicones; and the dispersion medium is a silicone oil exemplified above, with a higher preference given to the cases where the silicone oil is octamethyl cyclotetrasiloxane and decamethyl cyclopentasiloxane, from the viewpoints of the performance, stability and safety of the resulting ultraviolet shielding agents.

In the present invention, materials having no shielding abilities against the ultraviolet light may be contained in the ultraviolet shielding fine particles or the material dispersed therewith in an amount so as not to impair the optical properties of the ultraviolet shielding fine particles.

In the present invention, in the process of preparation of a starting material liquid mixture, a polar solvent having a good compatibility with the silicone oil may be further added, by which the coating of the particles comprising inorganic substances with the dispersant is more easily carried out. The easy coating is presumably owing to such effects of increasing adsorption to the surfaces of the particles by allowing the polar solvents to act on the polar functional groups of the dispersant. Further, a polar solvent may be added during or after a mill treatment and/or a high-pressure dispersion treatment. In particular, ethanol may be more preferably used as the polar solvent from the aspects of stability and safety. Also, the concentration of the polar solvent in the material dispersed with fine particles is preferably not more than 30% by weight.

In the present invention, in the process of preparing a material dispersed with the ultraviolet shielding fine particles by subjecting the starting material liquid mixture to a mill treatment and/or a high-pressure dispersion treatment, the silicone dispersant may be added in divided portions, by which the dispersibility of the ultraviolet shielding fine particles and the stability of the material dispersed with the ultraviolet shielding fine particles are improved. The methods for adding the silicone dispersants in divided portions are not particularly limited, and they may be suitably carried out depending upon the combinations of the particles comprising inorganic substances, the silicone dispersants, and the silicone oils, and amounts used therefor. Also, the methods for adding silicone dispersants may not be particularly limited, including the methods for continuously adding the silicone dispersants as well as the methods for adding the silicone dispersants in divided portions, which may be suitably carried out depending upon the combinations of the particles comprising inorganic substances, the silicone dispersants, and the silicone oils, and amounts used therefor.

2. Method for Producing Ultraviolet Shielding Fine Particles

Next, the method for producing the ultraviolet shielding fine particles of the present invention will be explained according to each of the steps described below.

There are the following two processes of the present invention for producing the desired products: (1) a material dispersed with the ultraviolet shielding fine particles obtained by dispersing the ultraviolet shielding fine particles in a silicone oil; and (2) a powdery product of the ultraviolet shielding fine particles obtained by drying the material dispersed with the ultraviolet shielding fine particles. Each of the processes comprises the following steps.

Specifically, (1) a method for producing a material dispersed with the ultraviolet shielding fine particles, comprises the step of:
 subjecting a starting material liquid mixture comprising particles comprising one or more inorganic substances having shielding abilities against the ultraviolet light, one or more silicone dispersants selected from modified silicones and reactive silicones, and a silicone oil to a mill treatment and/or a high-pressure dispersion treatment, to thereby form a material dispersed with the ultraviolet shielding fine particles.

(2) a method of producing a powdered product of a material dispersed with the above ultraviolet shielding fine particles, comprises the steps of:
 (a) subjecting a starting material liquid mixture comprising particles comprising one or more inorganic substances having shielding abilities against the ultraviolet light, one or more silicone dispersants selected from modified silicones and reactive silicones, and a silicone oil to a mill treatment and/or a high-pressure dispersion treatment, to thereby form a material dispersed with the ultraviolet shielding fine particles; and
 (b) drying the material dispersed with the ultraviolet shielding fine particles obtainable in step (a).

In step (a) mentioned above, it is desired that the starting material liquid mixture comprising the particles comprising inorganic substances having shielding abilities against the ultraviolet light, the silicone dispersants, and the silicone oil is subjected to a mill treatment and/or a high-pressure dispersion treatment to allow pulverization or disintegration of the particles comprising inorganic substances, whereby the dispersion state of the particles comprising inorganic substances in the starting material liquid mixture is maintained. Examples of mills include beads mills, sand mills, and ball mills, and examples of high-pressure dispersion devices include microfluidizers and nanomizers. The materials for media usable for mills, such as beads, sand, and balls, are preferably glass, zirconia, titania, and the like, and media sizes thereof are preferably 1 mm or less, more preferably 0.5 mm or less. Here, the particles comprising inorganic substances having shielding abilities against the ultraviolet light may be used in the forms of powdery products of fine particles and sols. In the case where a starting material liquid mixture having a high particle concentration is subjected to a mill treatment and/or a high-pressure dispersion treatment, a primary treatment is preferably carried out prior to the above treatments using a dispersion device capable of disintegrating fine particles, the dispersion devices including homomixers and homogenizers. The reasons for carrying out the primary treatment are that by disintegrating the fine particles having a high concentration, the fine particles being in an aggregated state, the load for the disintegration and dispersion required in secondary treatments subsequent to the above treatment, which may be a mill treatment and/or a high-pressure dispersion treatment, can be reduced, thereby making it possible to efficiently carry out the disintegration and dispersion. The concentration of the particles comprising inorganic substances in the starting material liquid mixture is preferably from 0.1 to 40% by weight, more preferably from 0.1 to 30% by weight, still more preferably from 0.1 to 27% by weight.

The amount of the dispersant used in the present invention is preferably from 1 to 200 parts by weight, based on 100 parts by weight of the particles comprising inorganic substances. The amount of the dispersant is more preferably from 1 to 100 parts by weight, still more preferably 1 to 60 parts by weight. When the amount of the dispersant is less than 1 part by weight, the amount of the dispersant becomes too small, so that the dispersibility cannot be exhibited, thereby making it difficult to inhibit the catalytic activities of the particles comprising inorganic substances. When the amount of the dispersant exceeds 200 parts by weight, the concentration of the dispersant becomes too high, so that the amount of the free dispersants which do not coat the surfaces of the fine particles is exceeding large, which rather causes inhibition of the dispersion of the fine particles in the material dispersed with the ultraviolet shielding fine particles, or increase in the viscosity of the material dispersed with the ultraviolet shielding fine particles.

Further, the material dispersed with the ultraviolet shielding fine particles obtained in step (a) can be concentrated.

In addition, the coating by the silicone dispersant may be carried out at the same time as the pulverization or disintegration of the particles in step (a).

The silicone dispersants usable in the present invention include one or more silicone compounds selected from the group consisting the modified silicones and reactive silicones exemplified above.

Next, the drying method employed in step (b) in the production processes for the powdery product of the ultraviolet shielding fine particles is not particularly limited. For example, as drying methods, such methods as hot-air drying and distillation treatments may be employed. More preferably, the resulting dried product may be pulverized. The pulverization method is not particularly limited, including, for example, such means as sand mills, blade-type mills, and counter jet mills. The fine particles obtained after pulverization may be classified to even up the particle sizes. In addition, drying and pulverization may be simultaneously carried, and means therefor are not particularly limited, including, for example, using a kneader, and the like.

In the present invention, it is important to uniformly disperse and blend the starting material liquid mixture by a mill treatment and/or a high-pressure dispersion treatment. In the present invention, there are the following cases: (1) the case where the fine particles consist of particles of only one kind of an inorganic substance; and (2) the case where the fine particles comprise particles of two or more kinds of inorganic substances.

(1) In the case where the fine particles consist of particles of only one kind of an inorganic substance, the primary particles thereof are aggregated predominantly by van der Waal's forces, the surfaces of which are coated with the dispersant.

(2) In the case where the fine particles comprise particles of two or more kinds of inorganic substances, the primary particles thereof are aggregated by electrostatic forces and van der Waal's forces, the surfaces of which are coated with the dispersant.

Here, in the case where the fine particles comprise particles of two or more kinds of inorganic substances, their compositional ratios may be suitably selected depending upon the relationship between the desired ultraviolet region to be shielded and the absorption end of the fine particles having the shielding abilities against the ultraviolet light.

By the method described above, the ultraviolet shielding fine particles, a material dispersed therewith, and a powdery product thereof can be obtained. In the present invention, for the purposes of firmly maintain the aggregated state of the aggregated particles and of reducing to substantially no catalytic activities of the particles comprising inorganic substances, the surfaces of each of the particles comprising inorganic substances and those of aggregated particles thereof are coated with a dispersant. The coating layer has a thickness of the level of substantially coating the active sites of the particle surfaces so that the surface activities do not affect the surrounding media of each of the particles comprising inorganic substances and aggregated particles thereof.

As described above, since the surface activities of the particles are substantially inhibited, the deterioration of the media (for instance, cosmetic base, coating, and the like) contacting the particle surfaces can be prevented. The problem of the catalytic activities is difficult to be avoided in cases where the particles comprising inorganic substances are used while dispersing them in various media. In the present invention, the means of solving the above problems is proposed. Incidentally, the principle of coating the particles comprising inorganic substances with the silicone dispersant may be physical adsorption or chemical adsorption. From the aspect of coating strength, the chemical adsorption is preferred.

The concentration of the ultraviolet shielding fine particles in the above material dispersed with the ultraviolet shielding fine particles is preferably from 0.1 to 40% by weight, more preferably from 0.1 to 30% by weight, still more preferably from 0.1 to 27% by weight. The reasons therefor are as follows. When the concentration of the fine particles in the material dispersed with the ultraviolet shielding fine particles is lower than 0.1% by weight, the amount of the fine particles becomes extremely small, thereby making it difficult to exhibit the optical properties owned by the fine particles. On the other hand, when the concentration is higher than 40% by weight, it is difficult to disperse the fine particles in the material dispersed with the ultraviolet shielding fine particles owing to their high concentration.

The shapes of the aggregated particles of the ultraviolet shielding fine particles dispersed in the above material dispersed with the ultraviolet shielding fine particles are not particularly limited. Also, the ultraviolet shielding fine particles have an average particle size of the dispersed particles of preferably from 0.01 to 5.0 $\mu$m, more preferably from 0.01 to 1.0 $\mu$m, still more preferably from 0.02 to 1.0 $\mu$m, particularly from 0.05 to 1.0 $\mu$m. Further, it is desired that the average particle size of the dispersed particles is still more preferably from 0.1 to 1.0 $\mu$m, particularly from 0.1 to 0.5 $\mu$m, and most preferably from 0.15 to 0.5 $\mu$m. In addition, it is preferred that the particle size distribution is as narrow as possible. When the average particle size exceeds 5.0 $\mu$m, the decrease in transparency and the decrease in the shielding abilities against the ultraviolet light drastically take place owing to the scattering of the visible light ascribed to the particle size effect. Incidentally, the observation of the shapes of the fine particles may be carried out using a transmission electron microscope, and the measurement of the particle size of the dispersed particles is carried out using a light-scattering type particle size analyzer (based on volume).

3. Material Dispersed with Ultraviolet Shielding Fine Particles and Powdery Products of Ultraviolet Shielding Fine Particles The material dispersed with the ultraviolet shielding fine particles and powdery products of the present invention can be obtained by the production methods described above, which have such a construction that the primary particles and the aggregated particles comprising aggregates of the primary particles are present in a mixed state, wherein these particles are coated with a dispersant. When the dispersibilities of these particles are poor, the optical properties of the fine particles are not likely to be exhibited. In addition, by having a coating layer formed by the dispersant mentioned above, the catalytic activities of the particles comprising inorganic substances can be substantially inhibited, so that the particles can be stably dispersed in a given medium without causing deterioration of the medium.

The shapes and the sizes of the powdery products of the ultraviolet shielding fine particles of the present invention are not particularly limited, and various shapes and sizes can be used according to different cases. For instance, when used as powdery products for cosmetics, spherical particles having a particle size ranging from sub-microns to ten micrometers are preferably used from the viewpoints of a good skin texture and easy handleability, and the plate-like particles having the same level of sizes given above are preferably used from the viewpoints of providing tackiness to the skin, spreadability on the skin, and handleability. Also, the silicone oils which are used for producing the material dispersed with the ultraviolet shielding fine particles can be used for the silicone oils for cosmetic base materials. In such cases, the resulting powdery products are free from the powdery texture, which is a specific skin texture which cannot be enjoyed by conventional inorganic ultraviolet shielding agents.

The optical properties of the material dispersed with the ultraviolet shielding fine particles or the powdery products of the ultraviolet shielding fine particles of the present invention can be quantitatively evaluated by measuring the light transmittance by ultraviolet-visible light spectroscopic analysis.

The preferred shielding abilities against the ultraviolet light for the ultraviolet shielding fine particles of the present invention are determined by measuring a light transmittance of not less than 80% at a wavelength of 800 nm, a light transmittance of not less than 15% at a wavelength of 400 nm, and a light transmittance of not more than 5% at least at one wavelength within the range from 380 nm to 300 nm, wherein the light transmittance is determined by suspending the material dispersed with the ultraviolet shielding fine particles or powdery products of the ultraviolet shielding fine particles in an oily agent and measuring light transmittance by an ultraviolet-visible light spectroscopy using an optical cell having an optical path length of 1 mm. By having the above properties, a high transparency particularly in the visible light region as well as a high shielding ability in the ultraviolet light region can be satisfactorily achieved.

The evaluation by ultraviolet-visible light spectroscopic analysis is carried out as concretely described below.

The material dispersed with the ultraviolet shielding fine particles or the powdery products of the ultraviolet shielding fine particles of the present invention are suspended in a silicone oil to prepare a suspension of fine particles having a given concentration so as to have a light transmittance of not less than 80% at a wavelength of 800 nm. In order to prepare a uniform suspension, the fine particles are stirred and well dispersed using, for instance, an ultrasonic disperser, etc. An optical cell having an optical path length of 1 mm is furnished and filled with the above suspension. An optical cell may be such that no absorption or no scattering of the light in the ultraviolet light region and the visible light region take place, and, for instance, a quartz cell can be used. The light transmittance of the light transmitting through the optical cell is measured using an ultraviolet-visible light spectrophotometer. In this method, a similar optical cell filled only with a medium before suspending the fine particles is used as a control to remove background.

Also, the ultraviolet shielding fine particles of the present invention have substantially no catalytic activities, which may be verified, for instance, by the following manner. Specifically, the ultraviolet shielding fine particles are dispersed in white vaseline so as to make the concentration of the particles comprising inorganic substances of 1% by weight, and the resulting mixture is subjected to a 60-minutes irradiation treatment with ultraviolet light having a central wavelength of 312 nm using an ultraviolet light source ("ENB-260C/J," manufactured by SPECTRONICS CORPORATION), to determine whether or not discoloration of white vaseline takes place in the resulting mixture. In the case where the white vaseline is adversely affected by the catalytic activities, a color change undergoes of from white to brown, and thus is easily verified by the above method.

Accordingly, in the present specification, the phrase "the ultraviolet shielding fine particles having substantially no catalytic activities" refers to the ultraviolet shielding fine particles whose catalytic activities are inhibited to such an extent that for practical purposes the catalytic activities pose no problems. For instance, when the catalytic activities are tested by the above method, no color changes of the vaseline are found.

4. Cosmetics

The cosmetics of the present invention may be prepared by optionally blending various kinds of adjuncts conventionally used for cosmetics, in addition to the above material dispersed with the ultraviolet shielding fine particles and the powdery products of the ultraviolet shielding fine particles. Examples thereof include the following:

(1) inorganic powders such as talc, kaolin, sericite, muscovite, phlogopite, lepidolite, biotite, synthetic golden mica, vermiculite, magnesium carbonate, calcium carbonate, diatomateous earth, magnesium silicate, calcium silicate, aluminum silicate, barium silicate, barium sulfate, strontium silicate, metallic tungustates, silica, hydroxyapatite, zeolite, boron nitride, and ceramic powders.

(2) organic powders such as nylon powders, polyethylene powders, polystyrene powders, benzoguanamine resin powders, polytetrafluoroethylene powders, distyrene-benzene polymer powders, epoxy resin powders, acrylic resin powders, and fine crystalline cellulose.

(3) inorganic white pigments such as titanium oxide and zinc oxide; inorganic red pigments such as iron oxide (red iron oxide) and iron titanate; inorganic brown pigments such as γ-iron oxide; inorganic yellow pigments such as yellow iron oxide and yellow ochre; inorganic black pigments such as black iron oxide and carbon black; inorganic violet pigments such as manganese violet and cobalt violet; inorganic green pigments such as chromium oxide, chromium hydroxide, and cobalt titanate; inorganic blue pigments such as ultramarine and Prussian blue; pearl-like pigments such as mica coated with titanium oxide, oxychlorobismuth coated with titanium oxide, oxychlorobismuth, talc coated with titanium oxide, fish scale flake, mica coated with colored titanium oxide; and metal powder pigments such as aluminum powders and copper powders.

(4) organic pigments including Pigment Red 201, Pigment Red 202, Pigment Red 204, Pigment Red 205, Pigment Red 220, Pigment Red 226, Pigment Red 228, Pigment Red 405, Pigment Orange 203, Pigment Orange 204, Pigment Yellow 205, Pigment Yellow 401, and Pigment Blue 404; organic pigments including zirconium lakes, barium lakes, and aluminum lakes of Pigment Red 3, Pigment Red 104, Pigment Red 106, Pigment Red 227, Pigment Red 230-(1), Pigment Red 230-(2), Pigment Red 401, Pigment Red 505, Pigment Orange 205, Pigment Yellow 4, Pigment Yellow 5, Pigment Yellow 202-(1), Pigment Yellow 202-(2), Pigment Yellow 203, Pigment Green 3, and Pigment Blue 1.

(5) natural pigments such as chlorophyll and β-carotene.

(6) various hydrocarbons, higher fatty acids, fats and oils, esters, higher alcohols, and waxes, such as squalane, paraffin wax, liquid paraffin, vaseline, microcrystalline wax, ozocerite, ceresine, myristic acid, palmitic acid, stearic acid, oleic acid, isostearic acid, cetyl alcohol, hexadecyl alcohol, oleyl alcohol, cetyl 2-ethylhexanoate, 2-ethylhexyl palmitate, 2-octyldodecyl myristate, neopentyl glycol di-2-ethylhexanoate, glycerol tri-2-ethylhexanoate, 2-octyldodecyl oleate, isopropyl myristate, glycerol triisostearate, coconut fatty acid triglyceride, olive oil, avocado oil, camellia oil, jojoba oil, beeswax, spermaceti, carnauba wax, myristyl myristate, mink oil, and lanoline; silicone oils such as volatile silicone oils and non-volatile silicone oils.

(7) The following ultraviolet protecting agents such as ultraviolet light absorbents may be optionally added in suitable amounts.

1) benzoic acid derivatives:

p-aminobenzoic acid (PABA), glycerol mono-p-aminobenzoate, ethyl p-N,N-dipropoxyaminobenzoate, ethyl p-N,N-diethoxyaminobenzoate, ethyl p-N,N-dimethylaminobenzoate, butyl p-N,N-dimethylaminobenzoate, amyl p-N,N-dimethylaminobenzoate, octyl p-N,N-dimethylaminobenzoate, and the like.

2) anthranilic acid derivatives:

homomenthyl N-acetylanthranilate, and the like.

3) salicylic acid derivatives:

amyl salicylate, menthyl salicylate, homomenthyl salicylate, octyl salicylate, phenyl salicylate, benzyl salicylate, p-isopropanolphenyl salicylate, and the like.

4) cinnamic acid derivatives:

octylcinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, glycerol mono-2-ethylhexanoyl-diparamethoxycinnamate, and the like.

5) benzophenone derivatives:
2,4-dihydroxybenzophenone, 2,2'-dihydroxy 4-methoxybenzophenone, 2,2'-dihydroxy 4,4'-dimethoxybenzophenone, 2,2',4,4'-tetrahydroxy benzophenone, 2-hydroxy 4-methoxybenzophenone, 2-hydroxy 4-methoxy-4'-methylbenzophenone, 2-hydroxy 4-methoxybenzophenon-5-sulfonate, 4-phenylbenzophenone, 2-ethylhexyl 4'-phenylbenzophenone-2-carboxylate, 2-hydroxy 4-n-octoxybenzophenone, 4-hydroxy 3-carboxybenzophenone, and the like.

6) other ultraviolet absorbents:
3-(4'-methylbenzylidene) d,l-camphor, 3-benzylidene d,l-camphor, urocanic acid, ethyl urocanate, 2-phenyl 5-methylbenzoxazole, 2,2'-hydroxy 5-methylphenylbenzotriazole, 2-(2'-hydroxy-5't-octylphenyl)benzotriazole, dibenzarsine, dianisoylmethane, 4-methoxy 4'-t-butyldibenzoylmethane, 5-(3,3'-dimethyl-2-norbornylidene)-3-pentan-2-one, 1-(3,4-dimethoxyphenyl)-4,4'-dimethyl-1,3-pentadione, and the like.

(8) Also, surfactants may be optionally used in suitable amounts.

Examples of the surfactants include polyoxyethylene alkyl ethers, polyoxyethylene fatty acid esters, polyoxyethylene sorbitan fatty acid esters, polyoxyethylene sorbitol fatty acid esters, alkyl polyoxyethylene hardened castor oil sulfates, alkyl polyoxyethylene sulfates, alkyl phosphates, alkyl polyoxyethylene phosphates, alkali metal salts of fatty acids, sorbitan fatty acid esters, glycerol fatty acid esters, and silicone-based surfactants, such as polyether-modified silicones.

(9) Further, water-soluble polyhydric alcohols may be optionally used in suitable amounts. Examples of the water-soluble polyhydric alcohols are water-soluble polyhydric alcohols having two or more hydroxyl groups in a molecule, including ethylene glycol, propylene glycol, 1,3-butylene glycol, 1,4-butylene glycol, dipropylene glycol, glycerol, polyglycerols, such as diglycerol, triglycerol, and tetraglycerol, glucose, maltose, maltitol, sucrose, fructose, xylitol, sorbitol, maltotriose, threitol, erythritol, and sugar alcohol derived from decomposed starch.

(10) In addition, other cosmetic adjuncts may be optionally added in suitable amounts, including amino acids, such as lysine and arginine; organic acids, such as lactic acid, citric acid, succinic acid, and glycolic acid, and organic salts thereof; resins, such as alkyd resins and urea resins; plasticizers, such as camphor and tributyl citrate; antioxidants, such as α-tocopherol; antiseptics, such as butyl p-hydroxybenzoate and methyl p-hydroxybenzoate; extracts from plants, such as cornflower, althea, and *Hypericuor erectum*; medicinal ingredients such as retinol and allantoin; binders such as xanthan gum and carrageenan; and perfumes.

In order to improve the skin texture and enjoy the continuity of the ultraviolet shielding effects, one or more silicone oils and ether-modified silicones may be incorporated in the cosmetics of the present invention.

The silicone oils are not particularly limited as long as they are those usually incorporated in cosmetics. Examples thereof include octamethyl polysiloxane, tetradecamethyl polysiloxane, methyl polysiloxane, high-polymerized methyl polysiloxane, methylphenyl polysiloxane, octamethyl cyclotetrasiloxane, decamethyl cyclopentasiloxane, trimethylsiloxysilicate, and organopolysiloxanes having a repeating unit represented by the general formula (1) or the general formula (2) mentioned above.

The amount of the silicone oils given above is from 2 to 80% by weight, preferably from 5 to 50% by weight, more preferably from 8 to 40% by weight in the cosmetic composition.

The ether-modified silicones are not particularly limited as long as they are compounds in which at least a part of the siloxane is substituted by a group having an ether bond. Examples thereof include the following, which may be used singly or in a combination of two or more kinds.

Concrete examples of the ether-modified silicones include the following compounds (I) to (III): (I) the ether-modified silicones having the following general formula (3):

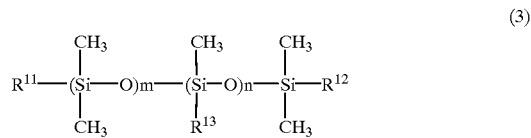

(3)

wherein at least one of $R^{11}$, $R^{12}$, and $R^{13}$ stands for a group having the general formula:

$R^{14}(OC_3H_6)_b(OC_2H_4)_aO(CH_2)_p—$, wherein $R^{14}$ stands for a hydrogen atom or an alkyl group having 1 to 12 carbon atoms; "a" and "b" independently stand for a number of from 0 to 35, "a" and "b" being average values; and p stands for a number of from 1 to 5, the remaining groups each stands for a methyl group; "m" and "n" are average values, wherein "m" stands for a number of from 1 to 200, and "n" stands for a number of from 0 to 50.

Among them, a preference is given to those having a molecular weight of from 2,000 to 50,000 wherein the amount occupied by substituents $R^{11}$ to $R^{13}$ is from 5 to 40%. Further, in the general formula (3), a preference given to the ether-modified silicones wherein "m" is from 5 to 80, "n" is from 0 to 2, "a" is from 9 to 10, "b" is equal to 0, "p" is equal to 3, and $R^{14}$ stands for a hydrogen atom, or the ether-modified silicones wherein "m" is from 90 to 110, "n" is equal to 0, "a" is from 11 to 13, "b" is equal to 0, "p" is equal to 3, and $R^{14}$ stands for a hydrogen atom.

Concrete examples of the ether-modified silicones represented by the general formula (3) above include commercially available products of the series of "SH-3775" manufactured by Toray-Dow Corning Corporation. (II) the polyether-alkyl-modified silicones having the following general formula (4):

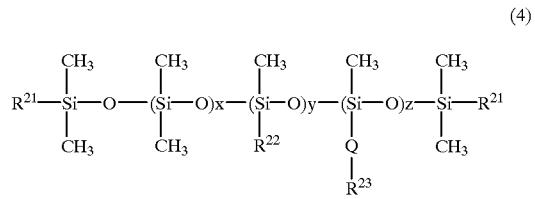

(4)

wherein $R^{21}$ stands for a hydrocarbon group having 1 to 5 carbon atoms, $R^{22}$ stands for a hydrocarbon group having 6 to 16 carbon atoms, Q stands for an alkylene group, $R^{23}$ stands for a group having the following formula:

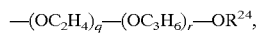

$—(OC_2H_4)_q—(OC_3H_6)_r—OR^{24}$, wherein $R^{24}$ stands for a hydrogen atom or a lower alkyl group, "q" and "r" each stands for a number satisfying the relationship of $q \leq r$, wherein the molecular weight of a $-(OC_2H_4)_q-(OC_3H_6)_r-$ moiety is from 600 to 3,500; z stands for a number of from 1 to 3; x and y each stands for a number satisfying the relationships of $x<3y$ and $x+y+z=30$ to 400, with proviso that the entire weight of the $-(OC_2H_4)_q-(OC_3H_6)_r-$ moiety does not exceed one-third of the entire weight of the polyether-alkyl-modified silicone having the general formula (4).

The hydrocarbon groups having 1 to 5 carbon atoms represented by $R^{21}$ in the general formula (4) include alkyl groups and alkenyl groups having 1 to 5 carbon atoms. Examples thereof include a methyl group, an ethyl group, a propyl group, an isopropyl group, a butyl group, a pentyl group, or a vinyl group, among which a preference is given to a methyl group. In addition, examples of the hydrocarbon groups having 6 to 16 carbon atoms represented by $R^{22}$ include linear alkyl groups, such as a hexyl group, a heptyl group, an octyl group, a nonyl group, a decyl group, an undecyl group, a dodecyl group, a tetradecyl group, a hexadecyl group; branched alkyl groups, such as an isooctyl group, an s-octyl group, and a 2-ethylhexyl group, among which a preference is given to a dodecyl group. Incidentally, in the case where y is greater than 1, $R^{22}$ may be identical or different for each of the repeating units.

Examples of the alkylene groups represented by Q in the general formula (4) include a methylene group, an ethylene group, a propylene group, a trimethylene group, and a tetramethylene group, among which a preference is given to a propylene group and a trimethylene group.

In the general formula (4), $R^{24}$, which is a group included in a group represented by $R^{23}$, stands for a hydrogen atom or a lower alkyl group (for instance, a methyl group, an ethyl group, a propyl group, an isopropyl group, or a butyl group), among which a preference is given to a hydrogen atom. In addition, preferred values of "q" and "r" are q=15 and r=0; or q=r=25; or q=29 and r=7.

Concrete examples of the polyether-alkyl-modified silicones having the general formula (4) include "DC Q2-2500," manufactured by Toray-Dow Corning Corporation (laurylmethycone copolyol, wherein $R^{21}$ stands for a methyl group, $R^{22}$ stands for a dodecyl group, and x is equal to 0 in the general formula (4). (III) the alkylglycerylether-modified silicones having the following general formula (5):

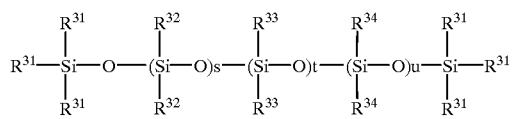

(5)

wherein at least one of $R^{31}$, $R^{32}$, $R^{33}$, and $R^{34}$ stands for a group having the general formula (6):

$$-A-OCH_2CH(OR^{41})CH_2OR^{42},$$

wherein A stands for a divalent hydrocarbon group having 3 to 20 carbon atoms; and $R^{41}$ and $R^{42}$ each independently stands for a hydrogen atom or a hydrocarbon group having 1 to 5 carbon atoms, with proviso that at least one of $R^{41}$ and $R^{42}$ is a hydrogen atom; and wherein the remaining groups each stands for a linear, branched, or cyclic hydrocarbon group having 1 to 30 carbon atoms, or a group having the following formula:

$$-BR^{43},$$

wherein B stands for a divalent hydrocarbon group having an ether bond and/or an ester bond; $R^{43}$ stands for a linear, branched, or cyclic hydrocarbon group having 1 to 30 carbon atoms; and wherein "s", "t", and "u" each stands for a number of from 0 to 200, and when s+t+u=0, one or more $R^{31}$ groups stand for a group having the general formula (6) defined above, excluding the case where at least one of $R^{31}$ having the general formula (6) is such that A stands for a trimethylene group, each of $R^{41}$ and $R^{42}$ stands for a hydrogen atom; and each of the remaining substituents of $R^{31}$, $R^{32}$, $R^{33}$, and $R^{34}$ stands for a methyl group.

Examples of the divalent hydrocarbon groups having 3 to 20 carbon atoms represented by A in the general formula (5) above include linear alkylene groups, such as a trimethylene group, a tetramethylene group, a pentamethylene group, a hexamethylene group, a heptamethylene group, an octamethylene group, a nonamethylene group, a decamethylene group, an undecamethylene group, a dodecamethylene group, a tetradecamethylene group, a hexadecamethylene group, and an octadecamethylene group; and branched alkylene groups, such as a propylene group, a 2-methyltrimethylene group, a 2-methyltetramethylene group, a 2-methylpentamethylene group, and a 3-pentamethylene group. Examples of the hydrocarbon groups having 1 to 5 carbon atoms represented by $R^{41}$ and $R^{42}$ include linear, branched, or cyclic alkyl groups, such as a methyl group, an ethyl group, a propyl group, an isopropyl group, a butyl group, a pentyl group, an s-butyl group, a t-butyl group, a neopentyl group, and a cyclopentyl group. Further, examples of the divalent hydrocarbon groups having an ether bond and/or an ester bond represented by B include groups having the following formulas:

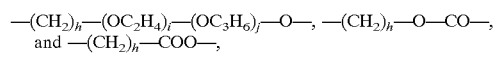

wherein "h" stands for an integer of from 3 to 20, and "i" and "j" each represents a number of from 0 to 50.

In addition, examples of the linear, branched, or cyclic hydrocarbon groups having 1 to 30 carbon atoms represented by $R^{43}$ include linear alkyl groups, such as a methyl group, an ethyl group, a propyl group, a butyl group, a pentyl group, a hexyl group, a heptyl group, an octyl group, a nonyl group, a decyl group, an undecyl group, a dodecyl group, a tetradodecyl group, a hexadecyl group, an octadecyl group, an eicosyl group, a doeicosyl, a tetraeicosyl group, a hexaeicosyl group, an octaeicosyl group, and a triacontyl group; branched alkyl groups, such as an isopropyl group, an s-butyl group, a t-butyl group, a neopentyl group, a 1-ethylpropyl group, and a 1-heptyldecyl group; and cyclic alkyl groups, such as a cyclopentyl group, a cyclohexyl group, an abietyl group, and a cholesteryl group.

The alkylglyceryl ether-modified silicones represented by the general formula (5) can be produced by the method disclosed in Japanese Patent Laid-Open No. 4-108795.

The amount of the ether-modified silicones given above is preferably from 0.05 to 20% by weight, particularly 1 to 10% by weight in the cosmetic composition.

Although an amount of the ultraviolet shielding fine particles of the present invention in the cosmetic composition depends upon the kinds of cosmetics produced, the amount is preferably 0.01 to 50% by weight, more preferably 0.05 to 40% by weight, particularly 0.1 to 30% by weight. When the amount of the ultraviolet shielding fine particles is less than the lower limit of the above range, sufficient shielding effects against the ultraviolet light cannot be achieved, and when the amount exceeds the upper limit of the above range, a pleasant skin texture when used as cosmetics are undesirably lost. The amount of the ultraviolet shielding fine particles when using a material dispersed with the ultraviolet shielding fine particles or powdery products thereof for cosmetics is determined so as to satisfy the amount specified in the cosmetics of the ultraviolet shielding fine particles mentioned above.

The cosmetics of the present invention may be formulated in various forms as conventionally prepared. Although the forms are not particularly limited, the cosmetics may be used as various make-up products including lotions, emulsions, creams, ointments, aerosol cosmetics, powdery foundations, powdery eyeshadows, emulsified foundations, and lipsticks.

SPF and PFA of the cosmetics of the present invention are measured by using an analyzer "SPF-290" (manufactured by The Optometrics Group) according to the basic measurement method described in the manual. Incidentally, PFA is indicated in the manual as "Average UV-A Protection Factor." From the viewpoint of sufficiently exhibiting the shielding effects in the ultraviolet region (B region), the SPF is preferably not less than 3, more preferably not less than 8, still more preferably not less than 10, and particularly not less than 13. From the viewpoint of sufficiently exhibiting the shielding effects of the ultraviolet region (A region) in the same manner as above, the PFA is preferably not less than 1.5.

The present invention will be described in further detail by means of the working examples of the present invention given hereinbelow, but the present invention is not limited by these examples. In the following working examples, the term "silicone oil dispersed with the fine particles" means a dispersed liquid of the ultraviolet shielding fine particles.

EXAMPLE 1

A solution comprising 25.0 g of an oxazoline-modified silicone ("OS96-20," manufactured by Kao Corporation) dissolved in 925.0 g of a silicone oil ("SH244," manufactured by Dow Corning Toray Silicone Co., Ltd.; refractive index: 1.39; a mixture of octamethylcyclotetrasiloxane and decamethylcyclopentasiloxane) was added to 50.0 g of powder of titanium oxide ultrafine particles ("MT-600B," manufactured by TAYCA CORPORATION; rutile-type; average particle size of primary particles: 0.05 $\mu$m), to give a starting material liquid mixture (Specifically, the concentration of $TiO_2$ in the starting material liquid mixture was 5% by weight, and the amount of the inorganic particles contained in the above starting material liquid mixture was 5% by weight.).

Using a mixed liquid comprising 325 g of glass beads ("BZ-01," manufactured by Iuchiseieido Co., Ltd.; average particle size: 0.1 mm) and 175 g of the prepared starting material liquid mixture, the resulting mixture was subjected to a treatment for 6 hours using a beads mill ("TSG-6H," manufactured by Igarashi Kikai Seizo Co., Ltd.) at an agitation rotational speed of 2000 r.p.m. Thereafter, the glass beads were removed to give a silicone oil dispersed with the $TiO_2$ fine particles (the concentration of the inorganic particle mixture being 5% by weight).

With the resulting silicone oil dispersed with the $TiO_2$ fine particles, the particle size of dispersed particles of the $TiO_2$ fine particles after the treatment was measured using a laser-doppler type particle size analyzer ("DLS-700," manufactured by OTSUKA ELECTRONICS CO., LTD.). It was found that the average particle size was about 0.20 $\mu$m (based on volume).

The dispersed $TiO_2$ fine particles after the treatment were observed using a transmission electron microscope. As a result, aggregates of $TiO_2$ ultrafine particles (average particle size (based on number): 0.05 $\mu$m) were found, which presumably had such a structure that the aggregates were coated with the oxazoline-modified silicone. In other words, the particles were aggregated particles of the $TiO_2$ (band gap energy: about 3.3 eV; refractive index: about 2.71) coated with the oxazoline-modified silicone.

The $TiO_2$ fine particles after the treatment were dispersed in white vaseline (manufactured by Wako Pure Chemical Industries, Ltd.), so as to have a concentration of the $TiO_2$ of 1% by weight in a mixture comprising white vaseline and the silicone oil dispersed with the $TiO_2$ fine particles. The resulting mixture was subjected to a 60-minute irradiation treatment with ultraviolet light having a central wavelength of 312 nm using an ultraviolet light source ("ENB-260C/J," manufactured by SPECTRONICS CORPORATION). As a result, for the dispersed liquid containing the $TiO_2$ fine particles, no color change of the white vaseline was observed, showing that the catalytic activities were substantially inhibited in the $TiO_2$ fine particles.

9.92 g of the silicone oil mentioned above was added to 0.08 g of the resulting silicone oil dispersed with the $TiO_2$ fine particles to allow dilution and dispersion. Thereafter, the light transmittance of the resulting dispersed liquid was measured by an ultraviolet-visible light spectrophotometer ("UV-160A," manufactured by Shimadzu Corporation) using a cell having an optical path length of 1 mm. The results are shown in FIG. 1.

In the figure, the light transmittance was 5% or less in the ultraviolet region B and the ultraviolet region C, the wavelengths of which were not longer than 320 nm. At the same time, the silicone oil dispersed with the fine particles showed remarkably high light transmittance values in the entire visible light region at a wavelength of from 400 to 800 nm, the light transmittance at 400 nm being 25%, and at 800 nm being 95%. Accordingly, the silicone oil dispersed with the $TiO_2$ fine particles thus produced had a high transparency in the visible light region and a high shielding ability in the ultraviolet region.

EXAMPLE 2

A solution comprising 17.5 g of an oxazoline-modified silicone (the same one as in Example 1) dissolved in 932.5 g of a silicone oil (the same one as in Example 1) was added to 50.0 g of powder of zinc oxide ultrafine particles ("FINEX 75," manufactured by Sakai Chemical Industry Co., Ltd.; average particle size of primary particles: 0.01 $\mu$m), to give a starting material liquid mixture (Specifically, the concentration of ZnO in the starting material liquid mixture was 5% by weight, and the amount of the inorganic particles contained in the above starting material liquid mixture was 5% by weight.).

Using a mixed liquid comprising 325 g of glass beads (the same one as in Example 1) and 175 g of the prepared starting material liquid mixture, the resulting mixture was subjected to a treatment for 6 hours using a beads mill (the same one as in Example 1) at an agitation rotational speed of 2000 r.p.m. Thereafter, the glass beads were removed to give a silicone oil dispersed with the ZnO fine particles (the concentration of the inorganic particle mixture being 5% by weight).

With the resulting silicone oil dispersed with the fine particles, the particle size of dispersed particles of the ZnO fine particles after the treatment was measured using a laser-doppler type particle size analyzer (the same one as in Example 1). It was found that the average particle size was about 0.21 $\mu$m (based on volume).

The ZnO fine particles after the treatment were observed using a transmission electron microscope. As a result, aggregates of ZnO ultrafine particles (average particle size (based on number): 0.01 μm) were found, which presumably had such a structure that the aggregates were coated with the oxazoline-modified silicone. In other words, the particles were aggregated particles of the ZnO (band gap energy: about 3.2 eV; refractive index: about 1.99) coated with the oxazoline-modified silicone.

The ZnO fine particles after the treatment were dispersed in white vaseline (the same one as in Example 1), so as to have a concentration of the ZnO of 1% by weight in a mixture comprising white vaseline and the silicone oil dispersed with the ZnO fine particles, and a test was carried out in the same manner as in Example 1. As a result, no color change of the white vaseline was observed, showing that the catalytic activities were substantially inhibited in the ZnO fine particles.

Figure 2:
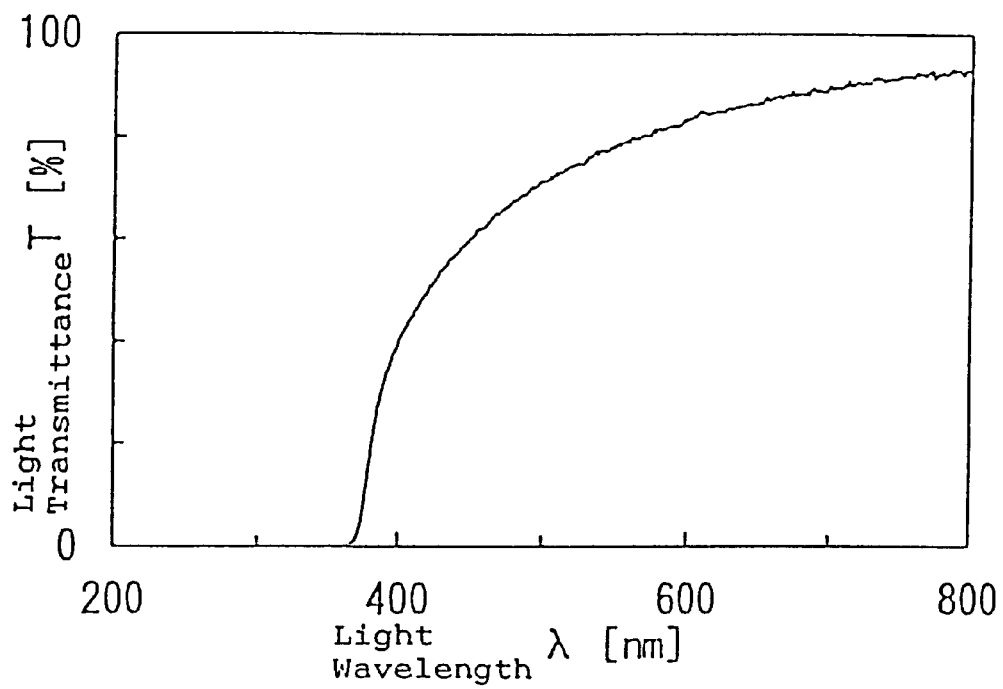
FIG. 2 is a chart showing the measurement results of the light transmittance of the material dispersed with ultraviolet shielding fine particles obtained in Example 2, as measured by an ultraviolet-visible light spectrophotometer.

9.5 g of the silicone oil mentioned above was added to 0.5 g of the resulting silicone oil dispersed with the ZnO fine particles to allow dilution and dispersion. Thereafter, the light transmittance of the resulting dispersed liquid was measured by a method similar to that of Example 1. The results are shown in FIG. 2.

In the figure, the light transmittance was 5% or less in the ultraviolet region B and the ultraviolet region C, the wavelengths of which were not longer than 320 nm. At the same time, the silicone oil dispersed with the fine particles showed remarkably high light transmittance values in the entire visible light region at a wavelength of from 400 to 800 nm, the light transmittance at 400 nm being 40%, and at 800 nm being 92%. Accordingly, the silicone oil dispersed with the ZnO fine particles thus produced had a high transparency in the visible light region and a high shielding ability in the ultraviolet region.

EXAMPLE 3

A solution comprising 10 g of an amino-modified silicone ("X-22-9261," manufactured by Shin-Etsu Silicone Corporation; molecular weight: 30000; and amino equivalency: 4980) dissolved in 940.0 g of a silicone oil (the same one as in Example 1) was added to 7.1 g of powder of titanium oxide ultrafine particles ("TTO-51(A)," manufactured by Ishihara Sangyo Kaisha, Ltd.; rutile-type; average particle size of primary particles: 0.03 μm), 42.9 g of powder of zinc oxide ultrafine particles ("FINEX 75," manufactured by Sakai Chemical Industry Co., Ltd.; average particle size of primary particles: 0.01 μm), to give a starting material liquid mixture (Specifically, the concentrations of $TiO_2$ and ZnO in the starting material liquid mixture were, respectively, 0.71% by weight and 4.29% by weight, and the amount of the inorganic particles contained in the above starting material liquid mixture was 5% by weight.).

Using a mixed liquid comprising 325 g of glass beads (the same one as in Example 1) and 175 g of the prepared starting material liquid mixture, the resulting mixture was subjected to a treatment for 6 hours using a beads mill (the same one as in Example 1) at an agitation rotational speed of 2000 r.p.m. Thereafter, the glass beads were removed to give a silicone oil dispersed with the $TiO_2$/ZnO fine particles (the concentration of the inorganic particle mixture being 5% by weight).

With the resulting silicone oil dispersed with the fine particles, the particle size of dispersed particles of the $TiO_2$/ZnO fine particles after the treatment was measured using a laser-doppler type particle size analyzer (the same one as in Example 1). It was found that the average particle size was about 0.21 μm (based on volume).

The fine particles after the treatment were observed using a transmission electron microscope. As a result, aggregates of $TiO_2$ ultrafine particles (average particle size (based on number): 0.03 μm) and ZnO ultrafine particles (average particle size (based on number): 0.01 μm) were found, which presumably had such a structure that the aggregates were dispersed in and supported thereby, and coated with the amino-modified silicone. In other words, the particles were $TiO_2$/ZnO fine particles comprising the $TiO_2$ (band gap energy: about 3.3 eV; refractive index: about 2.71) and the ZnO (band gap energy: about 3.2 eV; refractive index: about 1.99).

The proportions of each of the particles in the above fine particles were, respectively, 20.0% by volume and 80.0% by volume, each of which was calculated based on the compositional ratio of particles in the starting material liquid mixture, wherein particle densities of $TiO_2$ and ZnO were 3.84 g/cm$^3$ and 5.78 g/cm$^3$, respectively. The refractive index of the above fine particles was about 2.13, the refractive index being calculated based on the volume ratio of each of the particles.

The fine particles after the treatment were dispersed in white vaseline (the same one as in Example 1), so as to have a total concentration of the $TiO_2$ and the ZnO of 1% by weight in a mixture comprising white vaseline and the silicone oil dispersed with the fine particles, and a test was carried out in the same manner as in Example 1. As a result, no color change of the white vaseline was observed, showing that the catalytic activities were substantially inhibited in the $TiO_2$/ZnO fine particles.

Figure 3:
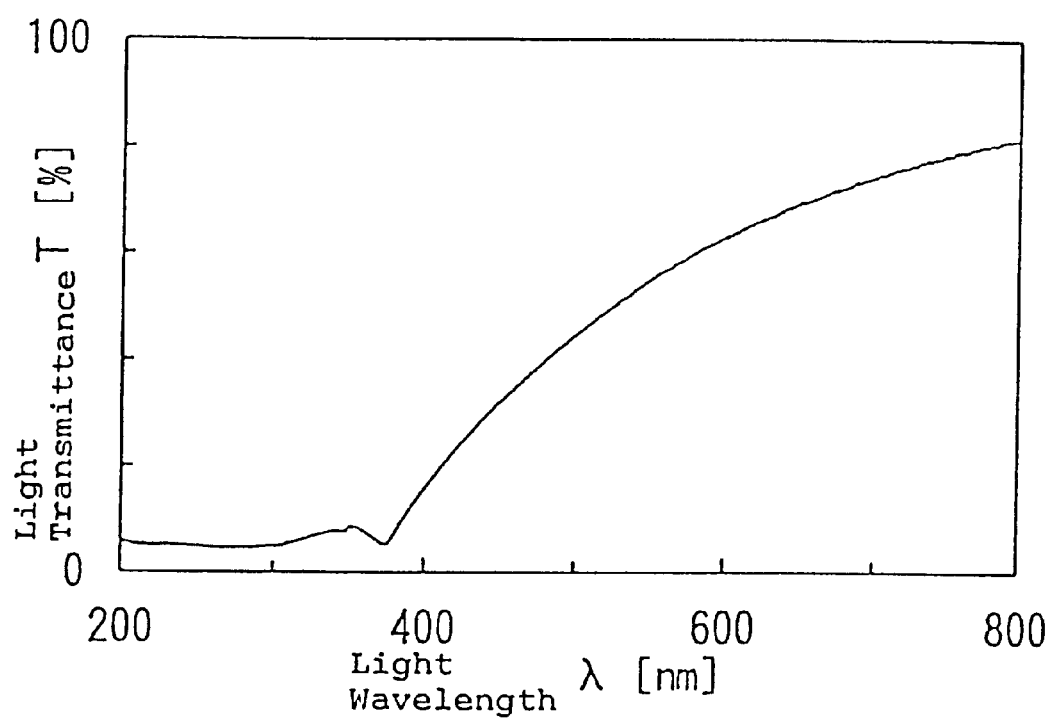
FIG. 3 is a chart showing the measurement results of the light transmittance of the material dispersed with ultraviolet shielding fine particles obtained in Example 3, as measured by an ultraviolet-visible light spectrophotometer.

9.82 g of the silicone oil mentioned above was added to 0.18 g of the resulting silicone oil dispersed with the $TiO_2$/ZnO fine particles to allow dilution and dispersion. Thereafter, the light transmittance of the resulting dispersed liquid was measured by a method similar to that of Example 1. The results are shown in FIG. 3.

In the figure, the light transmittance was 5% or less in the ultraviolet region B and the ultraviolet region C, the wavelengths of which were in the range of from 250 to 305 nm. At the same time, the silicone oil dispersed with the fine particles showed high light transmittance values in the entire visible light region at a wavelength of from 400 to 800 nm, the light transmittance at 400 nm being 16%, and at 800 nm being 81%. Accordingly, the silicone oil dispersed with the $TiO_2$/ZnO fine particles thus produced had a high transparency in the visible light region and a high shielding ability in the ultraviolet region.

EXAMPLE 4

A solution comprising 10 g of an oxazoline-modified silicone (the same one as in Example 1) dissolved in 940.0 g of a silicone oil (the same one as in Example 1) was added to 7.1 g of powder of titanium oxide ultrafine particles ("MT-600SA," manufactured by TAYCA CORPORATION; rutile-type; average particle size of primary particles: 0.05 μm) and 42.9 g of powder of zinc oxide ultrafine particles (fine zinc flower, manufactured by Sakai Chemical Industry Co., Ltd.; average particle size of primary particles: 0.2 μm), to give a starting material liquid mixture (Specifically, the concentrations of $TiO_2$ and ZnO in the starting material liquid mixture were, respectively, 0.71% by weight and 4.29% by weight, and the amount of the inorganic particles contained in the above starting material liquid mixture was 5% by weight.).

The prepared starting material liquid mixture was subjected to a pretreatment using a homogenizer ("T.

K.-ROBOMICS," manufactured by Tokushu Kika Kogyo Co., Ltd.) at 12000 r.p.m. for 90 minutes. Thereafter, while agitating at 7000 r.p.m., the pretreated starting material liquid mixture was further subjected to a dispersion treatment using a mill ("DYNO MILL KDL-PILOT," manufactured by Willy A. Bachofen AG) at an agitation rotational speed of 3600 r.p.m. and a solution:media ratio of 600 cc:1200 cc, for an average retention time for each run inside the DYNO MILL of 8 minutes, the treatment procedure being carried out three times, to give a silicone oil dispersed with the $TiO_2$/ZnO fine particles (the concentration of the inorganic particle mixture being 5% by weight).

The above silicone oil dispersed with the fine particles was subjected to a distillation treatment at 80° C. using a rotary evaporator, to thereby concentrate to have a fine particle concentration of about 12.5% by weight. Thereafter, the resulting mixture was dispersed for 15 minutes at 9000 r.p.m. using a homogenizer. Subsequently, the silicone oil dispersed with the fine particles was concentrated again by a distillation treatment at 80° C. using a rotary evaporator, and then the resulting mixture was dispersed for 15 minutes at 9000 r.p.m. using a homogenizer, to give a silicone oil dispersed with the fine particles (fine particles: 20.8% by weight).

With the resulting silicone oil dispersed with the $TiO_2$/ZnO fine particles, the particle size of dispersed particles after the treatment was measured using a laser-doppler type particle size analyzer (the same one as in Example 1). It was found that the average particle size was about 0.20 μm (based on volume).

The fine particles after the treatment were observed using a transmission electron microscope. As a result, aggregates of $TiO_2$ ultrafine particles (average particle size (based on number): 0.05 μm) and ZnO ultrafine particles (average particle size (based on number): about 0.06 μm) were found, which presumably had such a structure that the aggregates were dispersed in and supported thereby, and coated with the oxazoline-modified silicone. In other words, the particles were $TiO_2$/ZnO fine particles comprising the $TiO_2$ (band gap energy: about 3.3 eV; refractive index: about 2.71) and the ZnO (band gap energy: about 3.2 eV; refractive index: about 1.99).

The proportions of each of the particles in the above fine particles were, respectively, 20.0% by volume and 80.0% by volume, each of which was calculated based on the compositional ratio of particles in the starting material liquid mixture, wherein particle densities of $TiO_2$ and ZnO were 3.84 g/cm$^3$ and 5.78 g/cm$^3$, respectively. The refractive index of the above fine particles was about 2.13, the refractive index being calculated based on the volume ratio of each of the particles.

The fine particles after the treatment were dispersed in white vaseline (the same one as in Example 1), so as to have a total concentration of the $TiO_2$ and the ZnO of 1% by weight in a mixture comprising white vaseline and the silicone oil dispersed with the fine particles, and a test was carried out in the same manner as in Example 1. As a result, no color change of the white vaseline was observed, showing that the catalytic activities were substantially inhibited in the $TiO_2$/ZnO fine particles.

Figure 4:
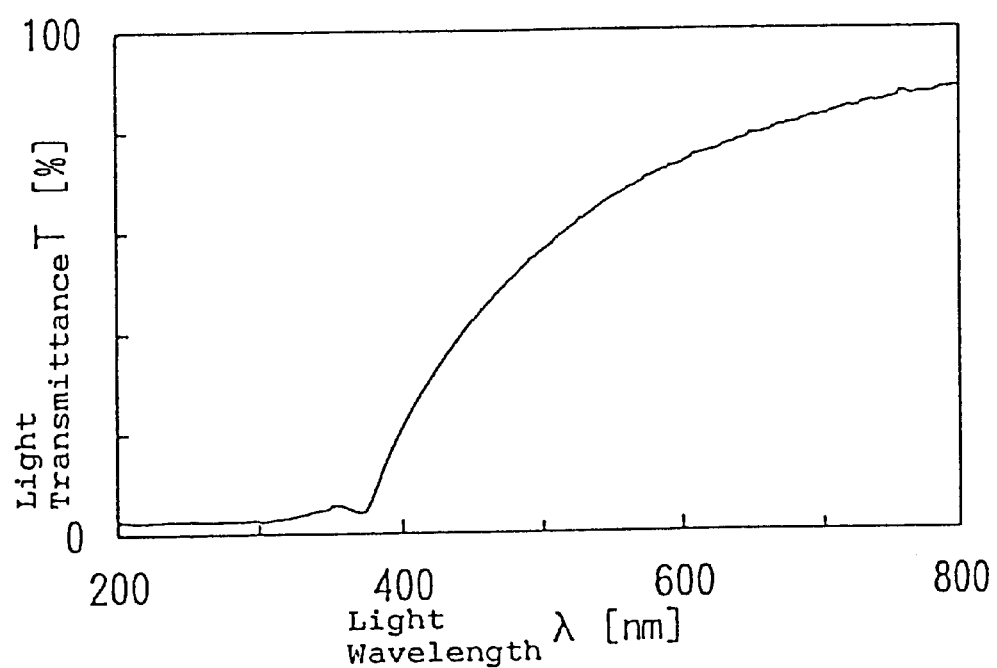
FIG. 4 is a chart showing the measurement results of the light transmittance of the material dispersed with ultraviolet shielding fine particles obtained in Example 4, as measured by an ultraviolet-visible light spectrophotometer.

9.957 g of the silicone oil mentioned above was added to 0.043 g of the resulting silicone oil dispersed with the $TiO_2$/ZnO fine particles to allow dilution and dispersion. Thereafter, the light transmittance of the resulting dispersed liquid was measured by a method similar to that of Example 1. The results are shown in FIG. 4.

In the figure, the light transmittance was 5% or less in the ultraviolet region B and the ultraviolet region C, the wavelengths of which were in the range of not longer than 320 nm. At the same time, the silicone oil dispersed with the $TiO_2$/ZnO fine particles showed high light transmittance values in the entire visible light region at a wavelength of from 400 to 800 nm, the light transmittance at 400 nm being 21%, and at 800 nm being 88%. Accordingly, the silicone oil dispersed with the $TiO_2$/ZnO fine particles thus produced had a high transparency in the visible light region and a high shielding ability in the ultraviolet region.

EXAMPLE 5

A solution comprising 12.5 g of an oxazoline-modified silicone (the same one as in Example 1) dissolved in 937.5 g of the silicone oil (the same one as in Example 1) was added to 7.1 g of powder of titanium oxide ultrafine particles ("TTO-51(A)," manufactured by Ishihara Sangyo Kaisha, Ltd.; rutile-type; average particle size of primary particles: 0.03 μm) and 42.9 g of powder of zinc oxide ultrafine particles ("FZN," manufactured by Kao Corporation; average particle size of primary particles: 0.15 μm), to give a starting material liquid mixture (Specifically, the concentrations of $TiO_2$ and ZnO in the starting material liquid mixture were, respectively, 0.71% by weight and 4.29% by weight, and the amount of the inorganic particles contained in the above starting material liquid mixture was 5% by weight.).

The prepared starting material liquid mixture was subjected to treatments in the same manner as in Example 4, to give a silicone oil dispersed with the $TiO_2$/ZnO fine particles (inorganic particle concentration: 5% by weight).

The above silicone oil dispersed with the fine particles was subjected to a distillation treatment at 80° C. using a rotary evaporator, to thereby concentrate to have a fine particle concentration of about 12% by weight. Thereafter, the resulting mixture was dispersed for 15 minutes at 9000 r.p.m. using a homogenizer. Subsequently, the silicone oil dispersed with the fine particles was concentrated again by a distillation treatment at 80° C. using a rotary evaporator, and then the resulting mixture was dispersed for 15 minutes at 9000 r.p.m. using a homogenizer, to give a silicone oil dispersed with the fine particles (fine particles: 20.8% by weight).

With the resulting silicone oil dispersed with the $TiO_2$/ZnO fine particles, the particle size of dispersed particles after the treatment was measured using a laser-doppler type particle size analyzer (the same one as in Example 1). It was found that the average particle size was about 0.25 μm (based on volume).

The fine particles after the treatment were observed using a transmission electron microscope. As a result, aggregates of $TiO_2$ ultrafine particles (average particle size (based on number): 0.03 μm) and ZnO ultrafine particles (average particle size (based on number): about 0.05 μm) were found, which presumably had such a structure that the aggregates were dispersed in and supported thereby, and coated with the oxazoline-modified silicone. In other words, the particles were $TiO_2$/ZnO fine particles comprising the $TiO_2$ (band gap energy: about 3.3 eV; refractive index: about 2.71) and the ZnO (band gap energy: about 3.2 eV; refractive index: about 1.99).

The proportions of each of the particles in the above fine particles were, respectively, 20.0% by volume and 80.0% by volume, each of which was calculated based on the compositional ratio of particles in the starting material liquid mixture, wherein particle densities of $TiO_2$ and ZnO were 3.84 g/cm$^3$ and 5.78 g/cm$^3$, respectively. The refractive index of the above fine particles was about 2.13, the refractive index being calculated based on the volume ratio of each of the particles.

The fine particles after the treatment were dispersed in white vaseline (the same one as in Example 1), so as to have a total concentration of the TiO$_2$ and the ZnO of 1% by weight in a mixture comprising white vaseline and the silicone oil dispersed with the fine particles, and a test was carried out in the same manner as in Example 1. As a result, no color change of the white vaseline was observed, showing that the catalytic activities were substantially inhibited in the TiO$_2$/ZnO fine particles.

Figure 5:
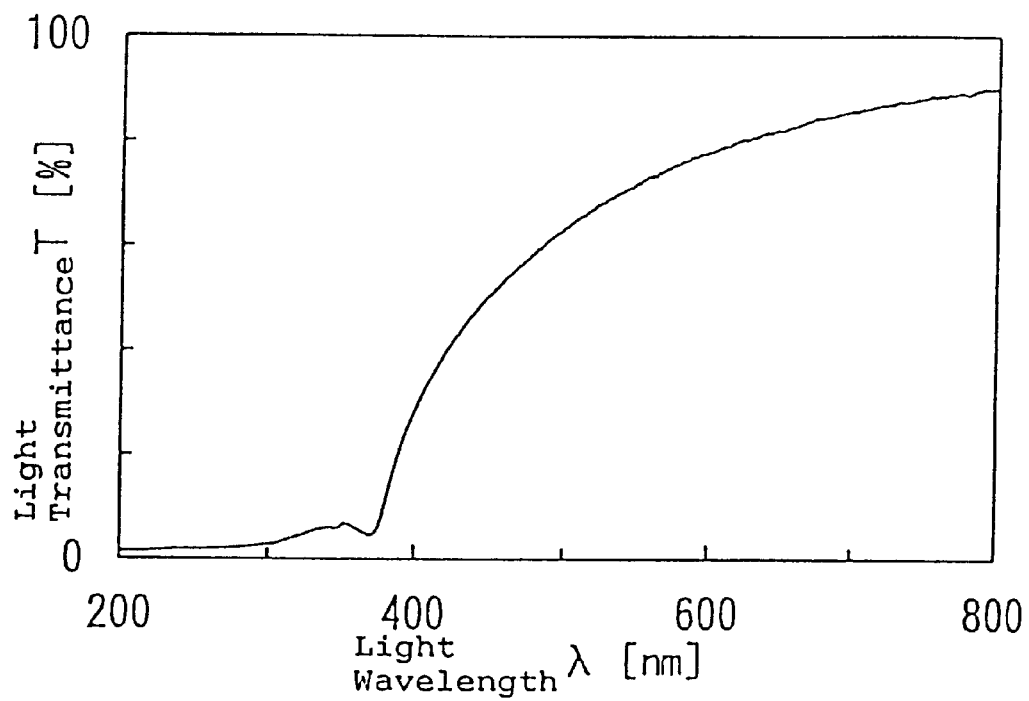
FIG. 5 is a chart showing the measurement results of the light transmittance of the material dispersed with ultraviolet shielding fine particles obtained in Example 5, as measured by an ultraviolet-visible light spectrophotometer.

9.955 g of the silicone oil mentioned above was added to 0.045 g of the resulting silicone oil dispersed with the TiO$_2$/ZnO fine particles to allow dilution and dispersion. Thereafter, the light transmittance of the resulting dispersed liquid was measured by a method similar to that of Example 1. The results are shown in FIG. 5.

In the figure, the light transmittance was 5% or less in the ultraviolet region B and the ultraviolet region C, the wavelengths of which were in the range of not longer than 320 nm. At the same time, the silicone oil dispersed with the TiO$_2$/ZnO fine particles showed high light transmittance values in the entire visible light region at a wavelength of from 400 to 800 nm, the light transmittance at 400 nm being 28%, and at 800 nm being 89%. Accordingly, the silicone oil dispersed with the TiO$_2$/ZnO fine particles thus produced had a high transparency in the visible light region and a high shielding ability in the ultraviolet region.

EXAMPLE 6

The preparation of the starting material liquid mixture and treatments therefor were carried out in the same manner as in Example 5, to give a silicone oil dispersed with the TiO$_2$/ZnO fine particles (inorganic particle concentration: 5% by weight).

The above silicone oil dispersed with the fine particles was dried using a vacuum dryer under the conditions of 50° C. and 300 Torr for 24 hours, to give a powdery product of fine particles.

The resulting powdery product of the TiO$_2$/ZnO fine particles was dispersed in the silicone oil (the same one as in Example 1), and the particle size of dispersed particles for the resulting powdery product of the fine particles after the treatment was measured using a laser-doppler type particle size analyzer (the same one as in Example 1). It was found that the average particle size was about 0.25 μm (based on volume).

The fine particles after the treatment were observed using a transmission electron microscope. As a result, aggregates of TiO$_2$ ultrafine particles (average particle size (based on number): 0.03 μm) and ZnO ultrafine particles (average particle size (based on number): about 0.05 μm) were found, which presumably had such a structure that the aggregates were dispersed in and supported thereby, and coated with the oxazoline-modified silicone. In other words, the particles are TiO$_2$/ZnO fine particles comprising the TiO$_2$ (band gap energy: about 3.3 eV; refractive index: about 2.71) and the ZnO (band gap energy: about 3.2 eV; refractive index: about 1.99).

The proportions of each of the particles in the above fine particles were, respectively, 20.0% by volume and 80.0% by volume, each of which was calculated based on the compositional ratio of particles in the starting material liquid mixture, wherein particle densities of TiO$_2$ and ZnO were 3.84 g/cm$^3$ and 5.78 g/cm$^3$, respectively. The refractive index of the above fine particles was about 2.13, the refractive index being calculated based on the volume ratio of each of the particles.

The fine particles after the treatment were dispersed in white vaseline (the same one as in Example 1), so as to have a total concentration of the TiO$_2$ and the ZnO of 1% by weight in a mixture comprising white vaseline and the powdery product of the fine particles, and a test was carried out in the same manner as in Example 1. As a result, no color change of the white vaseline was observed, showing that the catalytic activities were substantially inhibited in the TiO$_2$/ZnO fine particles.

Figure 6:
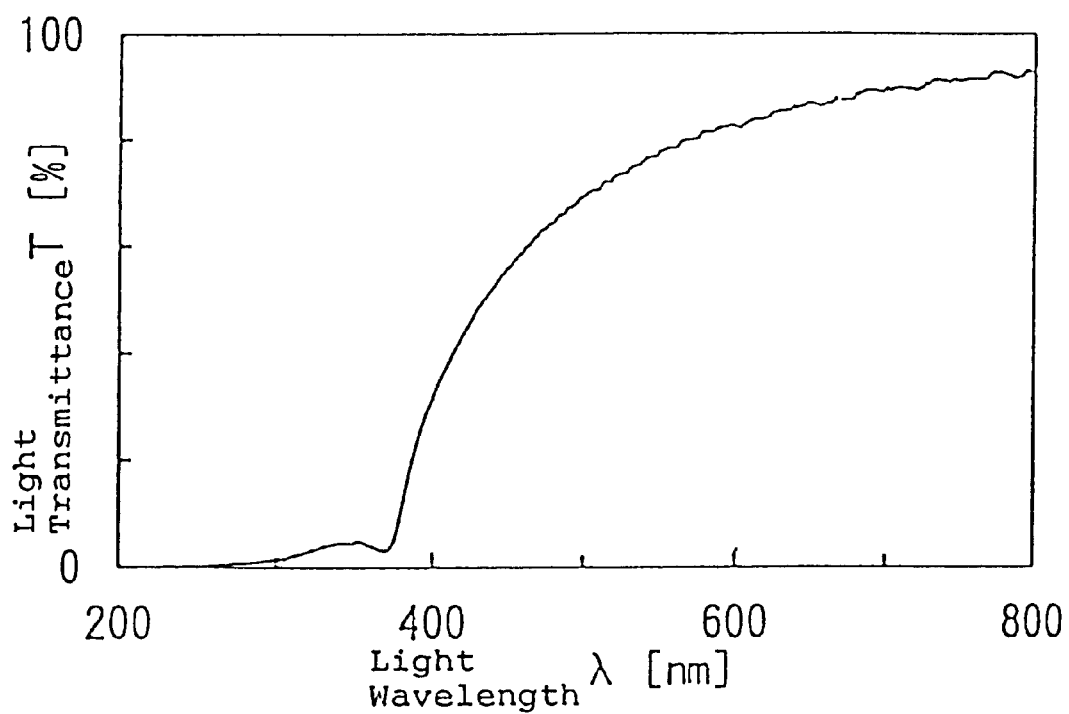
FIG. 6 is a chart showing the measurement results of the light transmittance of the material dispersed with ultraviolet shielding fine particles obtained in Example 6, as measured by an ultraviolet-visible light spectrophotometer.

9.985 g of the silicone oil mentioned above was added to 0.015 g of the resulting silicone oil dispersed with the TiO$_2$/ZnO fine particles to allow dilution and dispersion. Thereafter, the light transmittance of the resulting dispersed liquid was measured by a method similar to that of Example 1. The results are shown in FIG. 6.

In the figure, the light transmittance was 5% or less in the ultraviolet region B and the ultraviolet region C, the wavelengths of which were in the range of not longer than 320 nm. At the same time, the silicone oil dispersed with the TiO$_2$/ZnO fine particles showed high light transmittance values in the entire visible light region at a wavelength of from 400 to 800 nm, the light transmittance at 400 nm being 32%, and at 800 nm being 94%. Accordingly, the silicone oil dispersed with the TiO$_2$/ZnO fine particles thus produced had a high transparency in the visible light region and a high shielding ability in the ultraviolet region.

EXAMPLE 7

A solution comprising 58.3 g of an oxazoline-modified silicone ("OS88," manufactured by Kao Corporation) dissolved in 136.1 g of ethanol, and 2306 g of the silicone oil (the same one as in Example 1) were added to 83.3 g of powder of titanium oxide ultrafine particles ("TTO-51(A)," manufactured by Ishihara Sangyo Kaisha, Ltd.; rutile-type; average particle size of primary particles: 0.03 μm) and 500.0 g of powder of zinc oxide ultrafine particles (fine zinc flower, manufactured by Sakai Chemical Industry Co., Ltd.; average particle size of primary particles: 0.2 μm), to give a starting material liquid mixture (Specifically, the concentrations of TiO$_2$ and ZnO in the starting material liquid mixture were, respectively, 2.70% by weight and 16.21% by weight, and the amount of the inorganic particles contained in the above starting material liquid mixture was 18.91% by weight.).

The prepared starting material liquid mixture was subjected to a pretreatment using a homogenizer ("ULTRA-TARRAX T-50 (G45FF)," manufactured by IKA-MASCHINENBAU Janke & Kunkel GmbH & Co. KG) at 9000 r.p.m. for 10 minutes. Thereafter, while agitating at 1000 r.p.m., the pretreated starting material liquid mixture was further subjected to a dispersion treatment using a mill ("DYNO MILL KDL-PILOT," manufactured by Willy A. Bachofen AG) under the conditions of an agitation rotational speed of 3350 r.p.m. and a solution:media ("1113L (average partaicle size: 0.2 to 0.3 mm; undercut type)" manufactured by Union Co., Ltd.) ratio of 686 cc:1190 cc, for an average retention time inside the DYNO MILL for each run of 8 minutes, the treatment procedure being carried out three times, to give a silicone oil dispersed with the TiO$_2$/ZnO fine particles (inorganic particle concentration: 18.91% by weight).

With the resulting silicone oil dispersed with the TiO$_2$/ZnO fine particles, the particle size of dispersed particles after the treatment was measured using a laser-doppler type particle size analyzer (the same one as in Example 1). It was found that the average particle size was about 0.2 μm (based on volume).

The fine particles after the treatment were observed using a transmission electron microscope. As a result, aggregates of $TiO_2$ ultrafine particles (average particle size (based on number): 0.03 μm) and ZnO ultrafine particles (average particle size (based on number): about 0.06 μm) were found, which presumably had such a structure that the aggregates were dispersed in and supported thereby, and coated with the oxazoline-modified silicone. In other words, the particles were $TiO_2$/ZnO fine particles comprising the $TiO_2$ (band gap energy: about 3.3 eV; refractive index: about 2.71) and the ZnO (band gap energy: about 3.2 eV; refractive index: about 1.99).

The proportions of each of the particles in the above fine particles were, respectively, 20.0% by volume and 80.0% by volume, each of which was calculated based on the compositional ratio of particles in the starting material liquid mixture, wherein particle densities of $TiO_2$ and ZnO were 3.84 g/cm$^3$ and 5.78 g/cm$^3$, respectively. The refractive index of the above fine particles was about 2.13, the refractive index being calculated based on the volume ratio of each of the particles.

The fine particles after the treatment were dispersed in white vaseline (the same one as in Example 1), so as to have a total concentration of the $TiO_2$ and the ZnO of 1% by weight in a mixture comprising white vaseline and the silicone oil dispersed with the fine particles, and a test was carried out in the same manner as in Example 1. As a result, no color change of the white vaseline was observed, showing that the catalytic activities were substantially inhibited in the $TiO_2$/ZnO fine particles.

Figure 7:
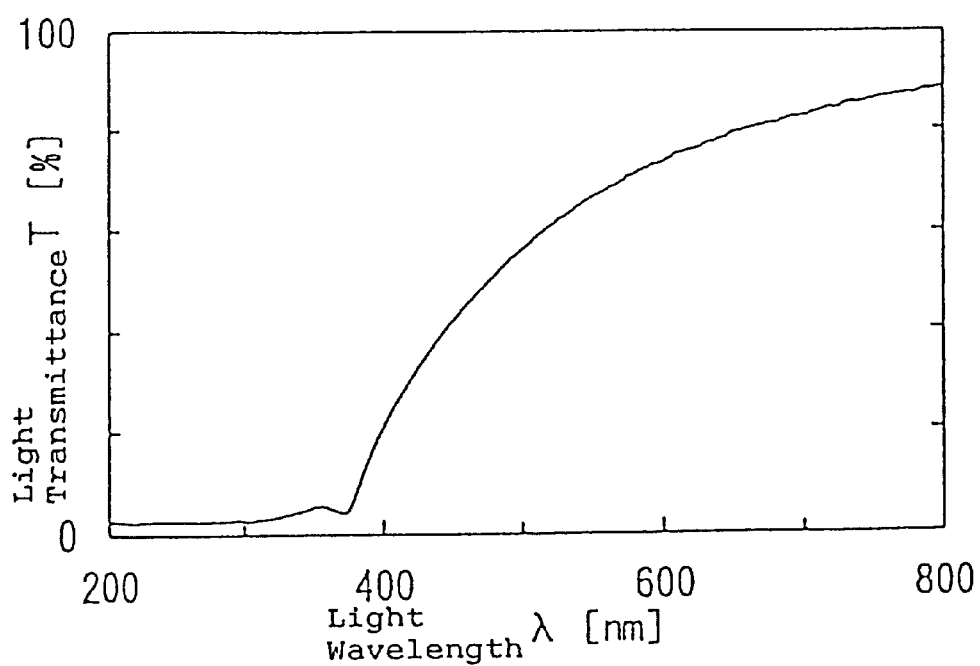
FIG. 7 is a chart showing the measurement results of the light transmittance of the material dispersed with ultraviolet shielding fine particles obtained in Example 7, as measured by an ultraviolet-visible light spectrophotometer.

9.967 g of the silicone oil mentioned above was added to 0.033 g of the resulting silicone oil dispersed with the $TiO_2$/ZnO fine particles to allow dilution and dispersion. Thereafter, the light transmittance of the resulting dispersed liquid was measured by a method similar to that of Example 1. The results are shown in FIG. 7.

In the figure, the light transmittance was 5% or less in the ultraviolet region B and the ultraviolet region C, the wavelengths of which were in the range of not longer than 320 nm. At the same time, the silicone oil dispersed with the $TiO_2$/ZnO fine particles showed high light transmittance values in the entire visible light region at a wavelength of from 400 to 800 nm, the light transmittance at 400 nm being 22%, and at 800 nm being 87%. Accordingly, the silicone oil dispersed with the $TiO_2$/ZnO fine particles thus produced had a high transparency in the visible light region and a high shielding ability in the ultraviolet region.

EXAMPLE 8

A solution comprising 87.5 g of an oxazoline-modified silicone ("OS88," manufactured by Kao Corporation) dissolved in 204.2 g of ethanol, and 2208.7 g of the silicone oil (the same one as in Example 1) were added to 83.3 g of powder of titanium oxide ultrafine particles ("TTO-51(A)," manufactured by Ishihara Sangyo Kaisha, Ltd.; rutile-type; average particle size of primary particles: 0.03 μm) and 500.0 g of powder of zinc oxide ultrafine particles (fine zinc flower, manufactured by Sakai Chemical Industry Co., Ltd.; average particle size of primary particles: 0.2 μm), to give a starting material liquid mixture (Specifically, the concentrations of $TiO_2$ and ZnO in the starting material liquid mixture were, respectively, 2.70% by weight and 16.21% by weight, and the amount of the inorganic particles contained in the above starting material liquid mixture was 18.91% by weight.).

The prepared starting material liquid mixture was subjected to a pretreatment using a homogenizer in the same manner as in Example 7. Thereafter, while agitating, the starting material liquid mixture was subjected to a further treatment using the DYNO MILL (average retention time inside the DYNO MILL of 8 minutes, the treatment procedure being carried out four times), to give a silicone oil dispersed with the $TiO_2$/ZnO fine particles (inorganic particle concentration: 18.91% by weight).

With the resulting silicone oil dispersed with the $TiO_2$/ZnO fine particles, the particle size of dispersed particles after the treatment was measured using a laser-doppler type particle size analyzer (the same one as in Example 1). It was found that the average particle size was about 0.2 μm (based on volume).

The fine particles after the treatment were observed using a transmission electron microscope. As a result, aggregates of $TiO_2$ ultrafine particles (average particle size (based on number): 0.03 μm) and ZnO ultrafine particles (average particle size (based on number): about 0.06 μm) were found, which presumably had such a structure that the aggregates were dispersed in and supported thereby, and coated with the oxazoline-modified silicone. In other words, the particles were $TiO_2$/ZnO fine particles comprising the $TiO_2$ (band gap energy: about 3.3 eV; refractive index: about 2.71) and the ZnO (band gap energy: about 3.2 eV; refractive index: about 1.99).

The proportions of each of the particles in the above fine particles were, respectively, 20.0% by volume and 80.0% by volume, each of which was calculated based on the compositional ratio of particles in the starting material liquid mixture, wherein particle densities of $TiO_2$ and ZnO were 3.84 g/cm$^3$ and 5.78 g/cm$^3$, respectively. The refractive index of the above fine particles was about 2.13, the refractive index being calculated based on the volume ratio of each of the particles.

The fine particles after the treatment were dispersed in white vaseline (the same one as in Example 1), so as to have a total concentration of the $TiO_2$ and the ZnO of 1% by weight in a mixture comprising white vaseline and the silicone oil dispersed with the fine particles, and a test was carried out in the same manner as in Example 1. As a result, no color change of the white vaseline was observed, showing that the catalytic activities were substantially inhibited in the $TiO_2$/ZnO fine particles.

Figure 8:
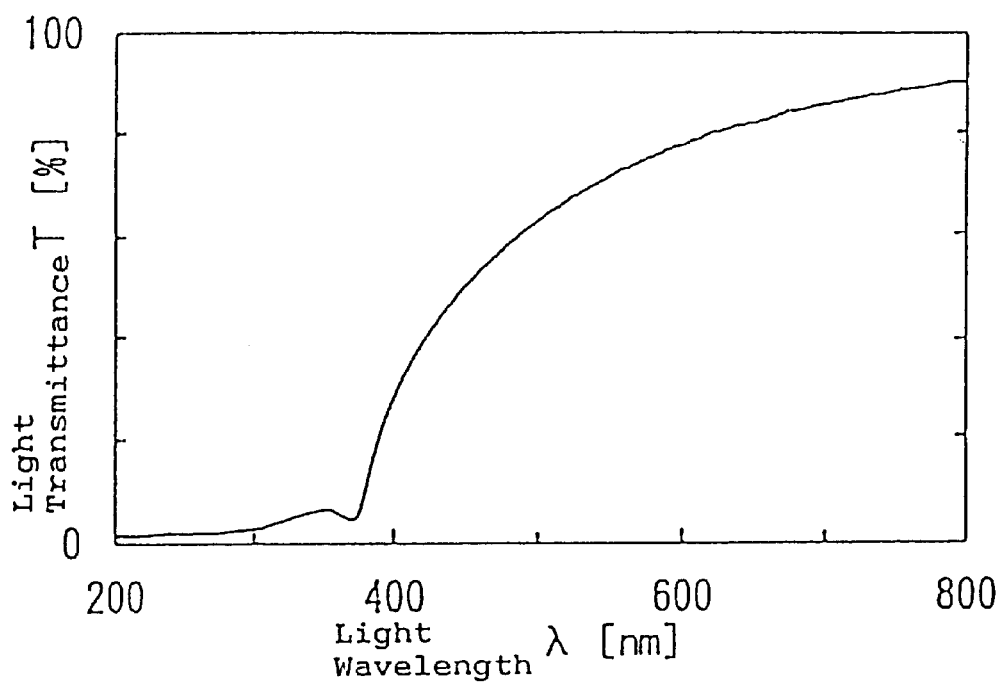
FIG. 8 is a chart showing the measurement results of the light transmittance of the material dispersed with ultraviolet shielding fine particles obtained in Example 8, as measured by an ultraviolet-visible light spectrophotometer.

9.967 g of the silicone oil mentioned above was added to 0.033 g of the resulting silicone oil dispersed with the $TiO_2$/ZnO fine particles to allow dilution and dispersion. Thereafter, the light transmittance of the resulting dispersed liquid was measured by a method similar to that of Example 1. The results are shown in FIG. 8.

In the figure, the light transmittance was 5% or less in the ultraviolet region B and the ultraviolet region C, the wavelengths of which were in the range of not longer than 320 nm. At the same time, the silicone oil dispersed with the $TiO_2$/ZnO fine particles showed high light transmittance values in the entire visible light region at a wavelength of from 400 to 800 nm, the light transmittance at 400 nm being 27%, and at 800 nm being 89%. Accordingly, the silicone oil dispersed with the $TiO_2$/ZnO fine particles thus produced had a high transparency in the visible light region and a high shielding ability in the ultraviolet region.

EXAMPLE 9

A solution comprising 100.0 g of an oxazoline-modified silicone ("OS88," manufactured by Kao Corporation) dissolved in 233.3 g of ethanol, and 2083.8 g of the silicone oil (the same one as in Example 1) were added to 83.3 g of powder of titanium oxide ultrafine particles ("TTO-51(A)," manufactured by Ishihara Sangyo Kaisha, Ltd.; rutile-type; average particle size of primary particles: 0.03 μm), 500.0 g of powder of zinc oxide ultrafine particles (fine zinc flower, manufactured by Sakai Chemical Industry Co., Ltd.; average particle size of primary particles: 0.2 μm), and 83.3 g of powder of silica ultrafine particle ("AEROSIL 300" manufactured by Nippon Aerozil Ltd.; average particle size of primary particles: 0.01 μm), to give a starting material liquid mixture (Specifically, the concentrations of $TiO_2$, ZnO, and $SiO_2$ in the starting material liquid mixture were, respectively, 2.70% by weight, 16.21% by weight, and 2.70% by weight, and the amount of the inorganic particles contained in the above starting material liquid mixture was 21.61% by weight.).

The prepared starting material liquid mixture was subjected to a pretreatment using a homogenizer in the same manner as in Example 7. Thereafter, while agitating, the starting material liquid mixture was subjected to a further treatment using the DYNO MILL (average retention time inside the DYNO MILL of 8 minutes, the treatment procedure being carried out three times), to give a silicone oil dispersed with the $TiO_2$/ZnO/$SiO_2$ fine particles (inorganic particle concentration: 21.61% by weight).

With the resulting silicone oil dispersed with the $TiO_2$/ZnO fine particles, the particle size of dispersed particles after the treatment was measured using a laser-doppler type particle size analyzer (the same one as in Example 1). It was found that the average particle size was about 0.2 μm (based on volume).

The fine particles after the treatment were observed using a transmission electron microscope. As a result, aggregates of $TiO_2$ ultrafine particles (average particle size (based on number): 0.03 μm), ZnO ultrafine particles (average particle size (based on number): about 0.06 μm), and $SiO_2$ (average particle size (based on number): about 0.01 μm) were found, which presumably had such a structure that the aggregates were dispersed in and supported thereby, and coated with the oxazoline-modified silicone. In other words, the particles were $TiO_2$/ZnO/$SiO_2$ fine particles comprising the $TiO_2$ (band gap energy: about 3.3 eV; refractive index: about 2.71), the ZnO (band gap energy: about 3.2 eV; refractive index: about 1.99), and the $SiO_2$ (band gap energy: about 6.4 eV; refractive index: about 1.46).

The proportions of each of the particles in the above fine particles were, respectively, 15.0% by volume, 59.7% by volume, and 25.3% by volume, each of which was calculated in the same manner as in Example 7 based on the compositional ratio of particles in the starting material liquid mixture, wherein particle densities of $TiO_2$, ZnO, and $SiO_2$ were 3.84 g/cm$^3$, 5.78 g/cm$^3$, and 2.27 g/cm$^3$, respectively. The refractive index of the above fine particles was about 1.96, the refractive index being calculated based on the volume ratio of each of the particles.

The fine particles after the treatment were dispersed in white vaseline (the same one as in Example 1), so as to have a total concentration of the $TiO_2$ and the ZnO of 1% by weight in a mixture comprising white vaseline and the silicone oil dispersed with the fine particles, and a test was carried out in the same manner as in Example 1. As a result, no color change of the white vaseline was observed, showing that the catalytic activities were substantially inhibited in the $TiO_2$/ZnO/$SiO_2$ fine particles.

Figure 9:
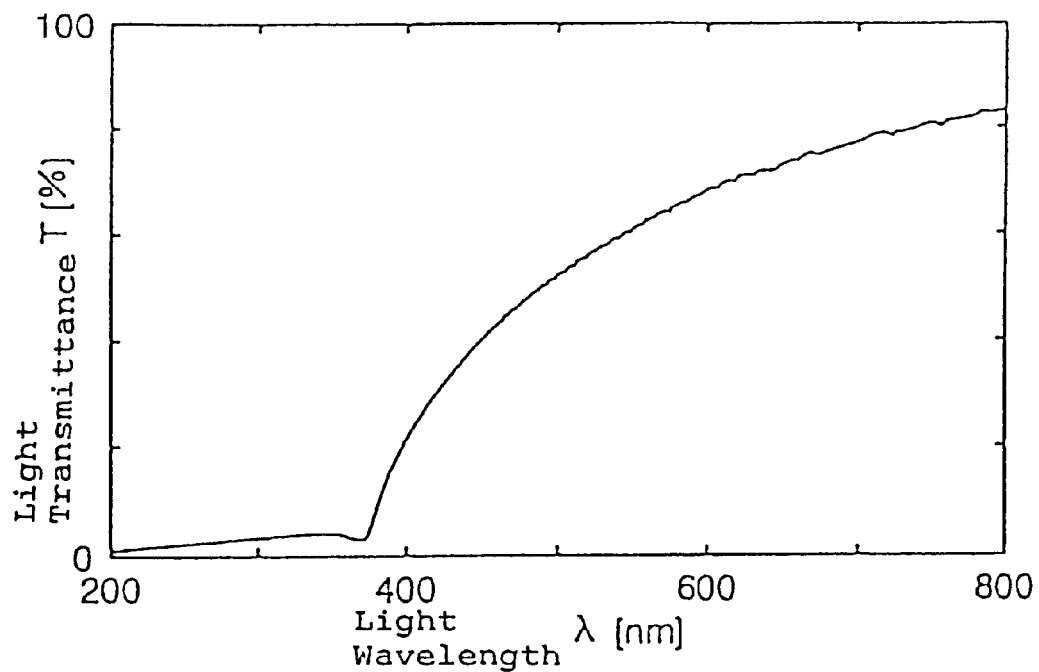
FIG. 9 shows the relationship between the light transmission and the wavelength.

9.944 g of the silicone oil mentioned above was added to 0.056 g of the resulting silicone oil dispersed with the $TiO_2$/ZnO/$SiO_2$ fine particles to allow dilution and dispersion. Thereafter, the light transmittance of the resulting dispersed liquid was measured by a method similar to that of Example 1. The results are shown in FIG. 9.

In the figure, the light transmittance was 5% or less in the ultraviolet region B and the ultraviolet region C, the wavelengths of which were in the range of not longer than 320 nm. At the same time, the silicone oil dispersed with the fine particles showed high light transmittance values in the entire visible light region at a wavelength of from 400 to 800 nm, the light transmittance at 400 nm being 21%, and at 800 nm being 83%. Accordingly, the silicone oil dispersed with the $TiO_2$/ZnO/$SiO_2$ fine particles thus produced had a high transparency in the visible light region and a high shielding ability in the ultraviolet region.

EXAMPLE 10

A solution comprising 187.5 g of a polyether-modified silicone ("SH3775," manufactured by Dow Corning Toray Silicone Co., Ltd.) dissolved in 1687.5 g of the silicone oil (the same one as in Example 1) was added to 125.0 g of powder of titanium oxide ultrafine particles ("TTO-51(A)," manufactured by Ishihara Sangyo Kaisha, Ltd.; rutile-type; average particle size of primary particles: 0.03 μm) and 500.0 g of powder of zinc oxide ultrafine particles ("FINEX 50", manufactured by Sakai Chemical Industry Co., Ltd.; average particle size of primary particles: 0.03 μm), to give a starting material liquid mixture (Specifically, the concentrations of $TiO_2$ and ZnO in the starting material liquid mixture were, respectively, 3.57% by weight and 21.4% by weight, and the amount of the inorganic particles contained in the above starting material liquid mixture was 25.0% by weight.).

The prepared starting material liquid mixture was subjected to treatments in the same manner as in Example 7, to give a silicone oil dispersed with the $TiO_2$/ZnO fine particles.

The particle size of dispersed particles in the resulting silicone oil dispersed with the fine particles after the treatment was measured in the same manner as in Example 1. As a result, it was found that the average particle size was about 0.15 μm (based on volume).

The silicone oil dispersed with the fine particles was dispersed in white vaseline, and a test was carried out in the same manner as in Example 1. As a result, no color change of the white vaseline was observed, showing that the catalytic activities were substantially inhibited in the $TiO_2$/ZnO fine particles.

9.975 g of the silicone oil mentioned above was added to 0.025 g of the resulting silicone oil dispersed with the $TiO_2$/ZnO fine particles to allow dilution and dispersion. Thereafter, the light transmittance of the resulting dispersed liquid was measured by a method similar to that of Example 1. As a result, it was found that the light transmittance was 5% or less in the ultraviolet region B and the ultraviolet region C, the wavelengths of which were in the range of not longer than 320 nm. At the same time, the silicone oil dispersed with the fine particles showed high light transmittance values in the entire visible light region at a wavelength of from 400 to 800 nm, the light transmittance at 400 nm being 45%, and at 800 nm being 85%. Accordingly, the silicone oil dispersed with the $TiO_2$/ZnO fine particles thus produced had a high transparency in the visible light region and a high shielding ability in the ultraviolet region.

EXAMPLE 11

A solution comprising 187.5 g of a polyether-modified silicone ("SH3775," manufactured by Dow Corning Toray Silicone Co., Ltd.) dissolved in 1270.8 g of the silicone oil (the same one as in Example 1) was added to 125.0 g of powder of titanium oxide ultrafine particles ("TTO-51(A)," manufactured by Ishihara Sangyo Kaisha, Ltd.; rutile-type; average particle size of primary particles: 0.03 μm) and 500.0 g of powder of zinc oxide ultrafine particles ("FINEX 50," manufactured by Sakai Chemical Industry Co., Ltd.; average particle size of primary particles: 0.03 μm), to give a starting material liquid mixture (Specifically, the concentrations of $TiO_2$ and ZnO in the starting material liquid mixture were, respectively, 4.29% by weight and 25.71% by weight, and the amount of the inorganic particles contained in the above starting material liquid mixture was 30.0% by weight.).

The prepared starting material liquid mixture was subjected to treatments in the same manner as in Example 7, to give a silicone oil dispersed with the $TiO_2$/ZnO fine particles.

The particle size of dispersed particles in the resulting silicone oil dispersed with the fine particles after the treatment was measured in the same manner as in Example 1. As a result, it was found that the average particle size was about 0.15 μm (based on volume).

The silicone oil dispersed with the fine particles was dispersed in white vaseline, and a test was carried out in the same manner as in Example 1. As a result, no color change of the white vaseline was observed, showing that the catalytic activities were substantially inhibited in the $TiO_2$/ZnO fine particles.

9.979 g of the silicone oil mentioned above was added to 0.021 g of the resulting silicone oil dispersed with the $TiO_2$/ZnO fine particles to allow dilution and dispersion. Thereafter, the light transmittance of the resulting dispersed liquid was measured by a method similar to that of Example 1. As a result, it was found that the light transmittance was 5% or less in the ultraviolet region B and the ultraviolet region C, the wavelengths of which were in the range of not longer than 320 nm. At the same time, the silicone oil dispersed with the $TiO_2$/ZnO fine particles showed high light transmittance values in the entire visible light region at a wavelength of from 400 to 800 nm, the light transmittance at 400 nm being 38%, and at 800 nm being 84%. Accordingly, the silicone oil dispersed with the $TiO_2$/ZnO fine particles thus produced had a high transparency in the visible light region and a high shielding ability in the ultraviolet region.

EXAMPLE 12

A solution comprising 125.0 g of an oxazoline-modified silicone ("OS88," manufactured by Kao Corporation) dissolved in 291.7 g of ethanol, and 2263.4 g of the silicone oil (the same one as in Example 1) were added to 125.0 g of powder of titanium oxide ultrafine particles ("RF-100," manufactured by Sakai Chemical Industry Co., Ltd.; rutile-type; average particle size of primary particles: 0.03 μm) and 500.0 g of powder of zinc oxide ultrafine particles ("PIGMOLITE ZINC OXIDE", manufactured by Daito Kasei Kogyo Co., Ltd; average particle size of primary particles: 0.2 μm), to give a starting material liquid mixture (Specifically, the concentrations of $TiO_2$ and ZnO in the starting material liquid mixture were, respectively, 2.70% by weight and 16.21% by weight, and the amount of the inorganic particles contained in the above starting material liquid mixture was 18.91% by weight.).

The prepared starting material liquid mixture was subjected to treatments in the same manner as in Example 7, to give a silicone oil dispersed with the $TiO_2$/ZnO fine particles.

The particle size of dispersed particles in the resulting silicone oil dispersed with the fine particles after the treatment was measured in the same manner as in Example 1. As a result, it was found that the average particle size was about 0.2 μm (based on volume).

The silicone oil dispersed with the fine particles was dispersed in white vaseline, and a test was carried out in the same manner as in Example 1. As a result, no color change of the white vaseline was observed, showing that the catalytic activities were substantially inhibited in the $TiO_2$/ZnO fine particles.

9.967 g of the silicone oil mentioned above was added to 0.033 g of the resulting silicone oil dispersed with the $TiO_2$/ZnO fine particles to allow dilution and dispersion. Thereafter, the light transmittance of the resulting dispersed liquid was measured by a method similar to that of Example 1. As a result, it was found that the light transmittance was 5% or less in the ultraviolet region B and the ultraviolet region C, the wavelengths of which were in the range of not longer than 320 nm. At the same time, the silicone oil dispersed with the $TiO_2$/ZnO fine particles showed high light transmittance values in the entire visible light region at a wavelength of from 400 to 800 nm, the light transmittance at 400 nm being 28%, and at 800 nm being 88%. Accordingly, the silicone oil dispersed with the $TiO_2$/ZnO fine particles thus produced had a high transparency in the visible light region and a high shielding ability in the ultraviolet region.

EXAMPLE 13

The treatments were carried out in the same manner as in Example 12 except for adding the oxazoline-modified silicone/ethanol solution in Example 12 in divided portions, to give a silicone oil dispersed with the $TiO_2$/ZnO fine particles (inorganic particle concentration: 18.9% by weight).

The particle size of the dispersed particles in the resulting silicone oil dispersed with the fine particles after the treatment was measured in the same manner as in Example 1. As a result, it was found that the average particle size was about 0.2 μm (based on volume).

The silicone oil dispersed with the fine particles was dispersed in white vaseline, and a test was carried out in the same manner as in Example 1. As a result, no color change of the white vaseline was observed, showing that the catalytic activities were substantially inhibited in the $TiO_2$/ZnO fine particles.

9.967 g of the silicone oil mentioned above was added to 0.033 g of the resulting silicone oil dispersed with the $TiO_2$/ZnO fine particles to allow dilution and dispersion. Thereafter, the light transmittance of the resulting dispersed liquid was measured by a method similar to that of Example 1. As a result, it was found that the light transmittance was 5% or less in the ultraviolet region B and the ultraviolet region C, the wavelengths of which were in the range of not longer than 320 nm. At the same time, the silicone oil dispersed with the fine particles showed high light transmittance values in the entire visible light region at a wavelength of from 400 to 800 nm, the light transmittance at 400 nm being 32%, and at 800 nm being 90%. Accordingly, the silicone oil dispersed with the $TiO_2$/ZnO fine particles thus produced had a high transparency in the visible light region and a high shielding ability in the ultraviolet region.

EXAMPLE 14

A solution comprising 50.0 g of an oxazoline-modified silicone ("OS96-20," manufactured by Kao Corporation)

dissolved in 900.0 g of a silicone oil ("SH244," manufactured by Dow Corning Toray Silicone Co., Ltd.; refractive index: 1.39) was added to 50.0 g of powder of titanium oxide ultrafine particles ("MT-600SA," manufactured by TAYCA CORPORATION; rutile-type; average particle size of primary particles: 0.05 μm), to give a starting material liquid mixture (Specifically, the concentration of $TiO_2$ in the starting material liquid mixture was 5% by weight, and the amount of the inorganic particles contained in the above starting material liquid mixture was 5% by weight.).

The prepared starting material liquid mixture was subjected to treatments in the same manner as in Example 1, to give a silicone oil dispersed with the $TiO_2$ fine particles.

The particle size of dispersed particles in the resulting silicone oil dispersed with the $TiO_2$ fine particles after the treatment was measured in the same manner as in Example 1. As a result, it was found that the average particle size was about 0.2 μm (based on volume).

The silicone oil dispersed with the fine particles was dispersed in white vaseline, and a test was carried out in the same manner as in Example 1. As a result, no color change of the white vaseline was observed, showing that the catalytic activities were substantially inhibited in the $TiO_2$ fine particles.

9.92 g of the silicone oil mentioned above was added to 0.08 g of the resulting silicone oil dispersed with the $TiO_2$ fine particles to allow dilution and dispersion. Thereafter, the light transmittance of the resulting dispersed liquid was measured by a method similar to that of Example 1. As a result, it was found that the light transmittance was 5% or less in the ultraviolet region B and the ultraviolet region C, the wavelengths of which were in the range of not longer than 320 nm. At the same time, the silicone oil dispersed with the fine particles showed high light transmittance values in the entire visible light region at a wavelength of from 400 to 800 nm, the light transmittance at 400 nm being 27%, and at 800 nm being 91%. Accordingly, the silicone oil dispersed with the $TiO_2$ fine particles thus produced had a high transparency in the visible light region and a high shielding ability in the ultraviolet region.

Comparative Example 1

The same procedures as in Example 3 were carried out except for using a methyl hydrogen polysiloxane ("KF99," manufactured by Shin-Etsu Silicone Corporation) as a dispersant. As a result, a uniform dispersion of the particles in the silicone oil could not be observed, entirely precipitating in the mixture.

Comparative Example 2

The same procedures as in Example 3 were carried out except for using caprylic glyceride (manufactured by Kao Corporation) as a dispersant. As a result, a uniform dispersion of the particles in the silicone oil could not be observed, entirely precipitating in the mixture.

Comparative Example 3

The same procedures as in Example 12 were carried out without using a dispersant. As a result, a uniform dispersion of the particles in the silicone oil could not be observed, entirely precipitating in the mixture.

Examples in which cosmetics are formulated are given hereinbelow.

SPF and PFA are measured by using an analyzer "SPF-290," manufactured by The Optometrics Group, according to the basic measurement method described in the manual. Incidentally, PFA is indicated in the manual as "Average UVA Protection Factor."

EXAMPLE 15

(Lotion)

| | | |
|---|---|---|
| Fine Particles of Example 10 | 15.0 | (weight %) |
| Ethanol | 30.0 | |
| Glycerol | 5.0 | |
| Polyethylene Glycol 1500 | 4.0 | |
| Polyoxyethylene(20) oleyl ether | 1.0 | |
| Polyoxyethylene(30) hydrogenated castor oil | 0.4 | |
| Urocanic acid | 1.0 | |
| Perfume | 0.1 | |
| Distilled Water | Balance | |

The lotion prepared by the above prescription was measured by an SPF analyzer. As a result, SPF was 3.2 and PFA was 1.7. It was found that skin after application was free from unnatural whitening, showing that the cosmetics had an excellent ultraviolet shielding effect.

EXAMPLE 16

(Emulsion)

| | | |
|---|---|---|
| Fine Particles of Example 11 | 20.0 | (weight %) |
| Cetanol | 1.2 | |
| Squalane | 2.0 | |
| Olive Oil | 4.5 | |
| Polyoxyethylene(10) hydrogenated castor oil | 1.0 | |
| Sorbitan monostearate | 1.0 | |
| Butyl p-hydroxybenzoate | 0.1 | |
| Methyl p-hydroxybenzoate | 0.1 | |
| Ethanol | 3.0 | |
| Glycerol | 2.0 | |
| 1,3-Butylene glycol | 2.0 | |
| Perfume | 0.1 | |
| Distilled Water | Balance | |

The emulsion prepared by the above prescription was measured by an SPF analyzer. As a result, SPF was 5.4 and PFA was 3.9. It was found that skin after application was free from unnatural whitening, showing that the cosmetics had an excellent ultraviolet shielding effect.

EXAMPLE 17

(Emulsion)

| | | |
|---|---|---|
| Fine Particles of Example 12 | 30.0 | (weight %) |
| Dimethylsiloxane-methyl(polyoxyethylene)-siloxane copolymer | 3.5 | |
| Octamethyltetracyclosiloxane | 20.0 | |
| Squalane | 2.0 | |
| Octyldodecyl myristate | 1.0 | |
| Butyl p-hydroxybenzoate | 0.1 | |
| Methyl p-hydroxybenzoate | 0.1 | |
| 2-Ethylhexyl p-methoxycinnamate | 4.0 | |
| Glycerol | 5.0 | |
| Perfume | 0.1 | |
| Distilled Water | Balance | |

The emulsion prepared by the above prescription was measured by an SPF analyzer. As a result, SPF was 16.5 and PFA was 5.5. It was found that skin after application was free from unnatural whitening, showing that the cosmetics had an excellent ultraviolet shielding effect.

EXAMPLE 18
(Cream)

| | | |
|---|---|---|
| Fine Particles of Example 13 | 30.0 | (weight %) |
| Dimethylsiloxane-methyl(polyoxyethylene)-siloxane copolymer | 4.0 | |
| Methyl polysiloxane (6 cSt) | 5.0 | |
| Octamethyltetracyclosiloxane | 10.0 | |
| Squalane | 2.0 | |
| Octyldodecyl myristate | 1.0 | |
| Butyl p-hydroxybenzoate | 0.1 | |
| Methyl p-hydroxybenzoate | 0.1 | |
| 2-Ethylhexyl p-methoxycinnamate | 3.0 | |
| Glycerol | 6.0 | |
| Perfume | 0.1 | |
| Distilled Water | Balance | |

The cream prepared by the above prescription was measured by an SPF analyzer. As a result, SPF was 18.5 and PFA was 5.3. It was found that skin after application was free from unnatural whitening, showing that the cosmetics had an excellent ultraviolet shielding effect.

EXAMPLE 19
(Powdery Foundation)

| | | | |
|---|---|---|---|
| (1) | Fine Particles of Example 11 | 5.0 | (weight %) |
| (2) | Fluorine Compound-Treated(*1) Mica | Balance | |
| (3) | Fluorine Compound-Treated(*1) Talc | 20.0 | |
| (4) | Fluorine Compound-Treated(*1) Titanium Oxide | 8.0 | |
| (5) | Fluorine Compound-Treated(*1) Iron Oxide (Red, Yellow, Black) | 3.0 | |
| (6) | Fluorine Compound-Treated(*1) Zinc Oxide Fine Particles | 2.0 | |
| (7) | Fluorine Compound-Treated(*1) Titanium Oxide Fine Particles | 1.0 | |
| (8) | Fluorine Compound-Treated(*1) Nylon Powder | 10.0 | |
| (9) | Dimethyl polysiloxane (10 cSt) | 4.0 | |
| (10) | Perfluoropolyether ("FOMBLIN HC-04") | 8.0 | |
| (11) | Hydrogenated Oil (Synchrowax) | 1.0 | |
| (12) | 2-Ethylhexyl p-methoxycinnamate | 1.0 | |
| (13) | Antiseptics, Perfume | 1.0 | |

Note
(*1)Those coated with 5% of perfluoroalkyl ethyl phosphate.

Ingredients (1) to (8) were blended in a Henschel mixer. Ingredients (9) to (13) subjected to blending and heating at 80° C. in advance were added to the mixture of the ingredients (1) to (8). The resulting mixture was pulverized using a pulverizer. A given amount of the pulverized product was taken out on a metallic pan and pressed by a pressing machine, to give a powdery foundation.

The resulting powdery foundation had high shielding effects against the ultraviolet light and had good spreadability, giving natural feeling after application.

EXAMPLE 20
(Two-Way Foundation)

| | | | |
|---|---|---|---|
| (1) | Fine Particles of Example 11 | 5.0 | (weight %) |
| (2) | Silicone-Treated(*2) Mica | Balance | |
| (3) | Silicone-Treated(*2) Talc | 20.0 | |
| (4) | Silicone-Treated(*2) Titanium Oxide | 9.0 | |
| (5) | Silicone-Treated(*2) Iron Oxide (Red, Yellow, Black) | 3.0 | |
| (6) | Silicone-Treated(*2) Zinc Oxide Fine Particles Coated with 30% of Nylon Powder | 8.0 | |
| (7) | Dimethyl polysiloxane (10,000 cSt) | 0.2 | |
| (8) | Dimethyl polysiloxane (6 cSt) | 8.0 | |
| (9) | 2-Ethylhexyl p-methoxycinnamate | 2.0 | |
| (10) | Hydrogenated Oil (Synchrowax) | 1.0 | |
| (11) | Antiseptics, Perfume | 1.0 | |

Note
(*2)Those coated with 2% of methylhydrogen polysiloxane.

Ingredients (1) to (6) were blended in a Henschel mixer. Ingredients (7) to (11) subjected to blending and heating at 80° C. in advance were added to the mixture of the ingredients (1) to (6). The resulting mixture was pulverized using a pulverizer. A given amount of the pulverized product was taken out on a metallic pan, and pressed by a pressing machine, to give a two-way foundation.

The resulting two-way foundation had high shielding effects against the ultraviolet light and had good spreadability, and natural feeling after application.

EXAMPLE 21
(Powdery Eye Shadow)

| | | | |
|---|---|---|---|
| (1) | Fine Particles of Example 12 | 12.0 | (weight %) |
| (2) | Lecithin-Treated(*3) Mica | Balance | |
| (3) | Lecithin-Treated(*3) Titanated Mica | 6.0 | |
| (4) | Silicone-Treated(*4) Ultramarine | 8.0 | |
| (5) | Silicone-Treated(*4) Prussian blue | 10.0 | |
| (6) | Silicone-Treated(*4) Iron Oxide (Red, Yellow, Black) | 2.0 | |
| (7) | Spherical Silicone Resin Powder ("TOSPEARL 145") | 10.0 | |
| (8) | Diisostearyl malate | 3.0 | |
| (9) | Hydrogenated Oil (Synchrowax) | 1.0 | |
| (10) | Vaseline | 1.0 | |
| (11) | Antiseptics, Perfume | 1.0 | |

Notes
(*3)Those coated with 5% of soybean lecithin.
(*4)Those coated with 2% of methylhydrogen polysiloxane.

Ingredients (1) to (7) were blended in a Henschel mixer. Ingredients (8) to (11) subjected to blending and heating at 80° C. in advance were added to the mixture of the ingredients (1) to (7). The resulting mixture was pulverized using a pulverizer. A given amount of the pulverized product was taken out on a metallic pan, and pressed by a pressing machine, to give a powdery eye shadow.

The resulting powdery eye shadow had high shielding effects against the ultraviolet light and had good spreadability, and provided good coloring to the skin.

EXAMPLE 22
(Emulsion Type's Foundation)

| | | | |
|---|---|---|---|
| (1) | Fine Particles of Example 13 | 30.0 | (weight %) |
| (2) | Silicone-Treated(*5) Titanium Oxide | 2.5 | |
| (3) | Silicone-Treated(*5) Iron Oxide (Red, Yellow, Black) | 1.0 | |
| (4) | Silicone-Treated(*5) Zinc Oxide Fine Particles | 3.0 | |
| (5) | Dimethylcyclopolysiloxane | 9.0 | |
| (6) | 2-Ethylhexyl p-methoxycinnamate | 2.0 | |
| (7) | Dimethylsiloxane-methyl-(polyoxyethylene)-siloxane copolymer | 1.0 | |

-continued

| | | |
|---|---|---|
| (8) Glycerol | 2.0 | |
| (9) Ethanol | 10.0 | |
| (10) Distilled water | Balance | |

Notes
(*5)Those coated with 2% of methylhydrogen polysiloxane.

Ingredients (1) to (4) were blended in a Henschel mixer. Ingredients (5) to (7) were separately blended, and the mixture of the ingredients (1) to (4) blended in advance was added to the mixture of the ingredients (5) to (7), and the obtained mixture was dispersed and mixed with a stirrer. A mixture of the ingredients (8) to (10) was gradually added over a period of 30 minutes to the above dispersed mixture while stirring. The obtained mixture was then emulsified by stirring with a homomixer for 10 minutes. The obtained emulsion was defoamed, and then a bottle was charged therewith to give an emulsion type's foundation.

The resulting emulsion type's foundation had high shielding effects against the ultraviolet light and good spreadability, and natural feeling after application.

EXAMPLE 23
(Lipstick)

| | | |
|---|---|---|
| (1) Fine Particles of Example 12 | 12.0 | (weight %) |
| (2) Silicone-Treated(*6) Red 201 | 1.0 | |
| (3) Silicone-Treated(*6) Red 202 | 1.0 | |
| (4) Silicone-Treated(*6) Yellow 4 Aluminum Lake | 1.0 | |
| (5) Silicone-Treated(*6) Titanium Oxide | 1.0 | |
| (6) Paraffin wax | 5.0 | |
| (7) Candelilla wax | 10.0 | |
| (8) Carnauba wax | 9.0 | |
| (9) Isopropyl isopalmitate | 20.0 | |
| (10) Isononyl isononanate | 15.0 | |
| (11) Isostearyl malate | 20.0 | |
| (12) Dimethyl polysiloxane (1000 cSt) | 5.0 | |

Note
(*6)Those coated with 2% of methylhydrogen polysiloxane.

Ingredients (1) to (12) were heated at 80° C. and blended to give a homogeneous mixture, and the obtained mixture was cooled to a temperature of 30° C. The cooled mixture was sufficiently blended with a triple roller, and then reheated to 80° C. The obtained mixture was casted into a mold and then solidified by cooling to give a lipstick.

The resulting lipstick had high shielding effects against the ultraviolet light and good spreadability, thus providing vivid coloration to the lip.

In the following working examples, as for the ether-modified silicones, the following five kinds of ether-modified silicones were used, without limiting the present invention to the following examples.

(i) Ether-modified silicone A:
Dimethylsiloxane-methyl (polyoxyethylene)siloxane copolymer represented by the general formula (3), with proviso that $R^{11}$ and $R^{12}$ both stand for methyl groups; $R^{13}$ stands for $H(OC_3H_6)_b(OC_2H_4)_aO(CH_2)_p$, wherein "a" is a number of from 7 to 15, "b" is equal to 0, and "p" is equal to 3; "m" is a number of from 50 to 100; and "n" is a number of from 1 to 5.

(ii) Ether-modified silicone B:
Dimethylsiloxane-methyl (polyoxyethylene)siloxane copolymer represented by the general formula (3), with proviso that $R^{11}$ and $R^{12}$ both stand for methyl groups; $R^{13}$ stands for $H(OC_3H_6)_b(OC_2H_4)_aO(CH_2)_p$, wherein "a" is a number of from 2 to 5, "b" is equal to 0, and "p" is equal to 3; "m" is a number of from 20 to 30; and "n" is a number of from 2 to 5.

(iii) Ether-modified silicone C:
Dimethylsiloxane-methyl (polyoxyethylene)siloxane copolymer represented by the general formula (3), with proviso that $R^{11}$ and $R^{12}$ both stand for methyl groups; $R^{13}$ stands for $H(OC_3H_6)_b(OC_2H_4)_aO(CH_2)_p$, wherein "a" is equal to 0, "b" is a number of from 7 to 13, and "p" is equal to 3; "m" is a number of from 4 to 10; and "n" is a number of from 1 to 6.

(iv) Ether-modified silicone D:
Laurylmethycone copolyol represented by the general formula (4), wherein $R^{21}$ stands for a methyl group; $R^{22}$ stands for a dodecyl group; $R^{23}$ stands for $-(OC_2H_4)_q(OC_3H_6)_r-OH$, wherein "q" is a number of from 10 to 30, and "r" is a number of from 10 to 30; Q stands for a trimethylene group; "x" is equal to 0; "y" is a number of from 30 to 70; and "z" is a number of from 1 to 6.

(v) Ether-modified silicone E:
Alkylglycerylether-modified silicones represented by the general formula (5), with proviso that at least one of $R^{34}$ stands for $-A-OCH_2CH(OR^{41})CH_2OR^{42}$, wherein "A" stands for $C_{11}H_{23}$; and $R^{41}$ and $R^{42}$ both stand for a hydrogen atom; "s" and "t" are numbers where the sum thereof equals to 60; "u" is equal to 4.

EXAMPLE 24
(Cream)

| | | |
|---|---|---|
| 1) Fine Particles of Example 11 | 30.0 | (weight %) |
| 2) Ether-modified silicone A ("SH-3775C," manufactured by Toray-Dow Corning) | 1.5 | |
| 3) α-Monomethyl-branched isostearyl glyceryl ether | 2.0 | |
| 4) Methyl polysiloxane (6 cSt) | 6.0 | |
| 5) 2-Ethylhexyl p-methoxycinnamate | 4.0 | |
| 6) Magnesium sulfate | 0.5 | |
| 7) Glycerol | 5.0 | |
| 8) Butyl p-hydroxybenzoate | 0.1 | |
| 9) Methyl p-hydroxybenzoate | 0.1 | |
| 10) Perfume | 0.05 | |
| 11) Distilled water | Balance | |

The cream having the above composition was measured using an SPF analyzer. As a result, SPF was 23.0 and PFA was 9.5.

It was found that skin after application was free from unnatural whitening, showing that the cosmetics had an excellent ultraviolet shielding effect.

EXAMPLE 25
(Emulsion)

| | | |
|---|---|---|
| 1) Fine Particles of Example 13 | 30.0 | (weight %) |
| 2) Ether-modified silicone C ("FZ-2110C," manufactured by Nippon Unicar) | 1.0 | |
| 3) Ether-modified silicone B ("KF-6015," manufactured by Shin-Etsu Silicone) | 2.0 | |
| 4) Ether-modified silicone D ("DC Q2-2500," manufactured by Toray-Dow Corning) | 1.0 | |
| 5) Methyl polysiloxane (6 cSt) | 4.0 | |

-continued

| | | |
|---|---|---|
| 6) Decamethyl cyclopentasiloxane | 6.0 | |
| 7) 2-Ethylhexyl p-methoxycinnamate | 3.0 | |
| 8) Squalane | 1.5 | |
| 7) Glycerol | 4.0 | |
| 8) Butyl p-hydroxybenzoate | 0.1 | |
| 9) Methyl p-hydroxybenzoate | 0.1 | |
| 10) Perfume | 0.05 | |
| 11) Distilled water | Balance | |

The emulsion having the above composition was measured using an SPF analyzer. As a result, SPF was 19.0 and PFA was 8.5.

It was found that skin after application was free from unnatural whitening.

EXAMPLE 26
(Cream)

| | | |
|---|---|---|
| 1) Fine Particles of Example 12 | 25.0 | (weight %) |
| 2) Ether-modified silicone E | 1.5 | |
| 3) Ether-modified silicone B ("KF-6015," manufactured by Shin-Etsu Silicone) | 0.5 | |
| 4) Methyl polysiloxane (6 cSt) | 6.0 | |
| 5) Decamethyl cyclopentasiloxane | 5.0 | |
| 6) 2-Ethylhexyl p-methoxycinnamate | 3.5 | |
| 7) 4-Methoxy-4'-t-butylbenzoylmethane | 2.0 | |
| 8) Squalane | 1.5 | |
| 9) Magnesium sulfate | 0.5 | |
| 10) Glycerol | 6.0 | |
| 11) Butyl p-hydroxybenzoate | 0.1 | |
| 12) Methyl p-hydroxybenzoate | 0.1 | |
| 13) Perfume | 0.05 | |
| 14) Distilled water | Balance | |

The cream having the above composition was measured using an SPF analyzer. As a result, SPF was 17.8 and PFA was 10.5.

It was found that skin after application was free from unnatural whitening.

Industrial Applicability

The material dispersed with the ultraviolet shielding fine particles in the present invention may be produced by a simple method comprising the step of subjecting a starting material liquid mixture comprising particles comprising one or more inorganic substances having shielding abilities against the ultraviolet light, one or more silicone dispersants selected from modified silicones and reactive silicones, and a silicone oil, to a mill treatment and/or a high-pressure dispersion treatment. Also, a powdery product of the ultraviolet shielding fine particles in the present invention may be produced by a simple method comprising the step of drying the material dispersed with the ultraviolet shielding fine particles obtainable by the above method.

The material dispersed with the ultraviolet shielding fine particles obtainable by the above method exhibits scattering ability and absorption ability ascribed to the fine particles in the ultraviolet light region, thereby showing high shielding abilities. In addition, by coating the surfaces of the ultraviolet shielding fine particles having high catalytic activities with a dispersant having substantially no catalytic activities, the surrounding media and the like are not likely to undergo deterioration by the catalytic activities owned by the ultraviolet shielding fine particles. Also, the powdery product of the ultraviolet shielding fine particles exhibits scattering ability and absorption ability by the fine particles in the ultraviolet light region when dispersed in a liquid or solid medium, thereby showing high shielding abilities. In addition, by coating the surfaces of the ultraviolet shielding fine particles having high catalytic activities with a dispersant having substantially no catalytic activities, the surrounding media and the like are not likely to undergo deterioration by the catalytic activities owned by the ultraviolet shielding fine particles.

In other words, since the material dispersed with the ultraviolet shielding fine particles and the powdery product of the ultraviolet shielding fine particles in the present invention comprise particles comprising inorganic substances having shielding abilities against the ultraviolet light and surfaces of the fine particles are coated with the silicone dispersant having substantially no catalytic activities, the resulting product has substantially no catalytic activities, thereby having high shielding abilities in the ultraviolet light region and easy handleability. Also, in the ultraviolet shielding fine particles in the present invention, since the surfaces of the particles are coated by silicone dispersant, the resulting product uniformly and stably disperses when formulated in an oil-based cosmetics, so that the deterioration of the cosmetic base material is not likely to take place. When these fine particles are formulated in cosmetics, those cosmetics have good smoothness, excellent spreadability on skin, no unevenness, excellent transparency, no unnatural skin whitening, high shielding effects against the ultraviolet light, and high safety and stability. Further, since the ultraviolet shielding fine particles of the present invention have excellent transparency, the coloration of the cosmetics is not impaired, having a high degree of freedom in the formulation amount in cosmetics.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for producing a material dispersed with ultraviolet shielding fine particles, comprising subjecting a starting material liquid mixture comprising particles comprising one or more inorganic substances having shielding abilities against ultraviolet light, one or more silicone dispersants selected from the group consisting of modified silicones and reactive silicones, and a silicone oil as dispersion media to a mill treatment and/or a high-pressure dispersion treatment to disperse the ultraviolet shielding fine particles in the silicone oil, wherein the ultraviolet shielding fine particles are dispersed in the silicone oil, wherein said ultraviolet shielding fine particles have substantially no catalytic activity, and wherein a polar solvent having good compatibility with said silicone oil is further added in at least one step selected from the group consisting of, (a) process for the preparation of the starting material liquid mixture;

(b) during the mill treatment or high-pressure dispersion treatment; and (c) after the mill treatment or high-pressure dispersion treatment.

2. The method for producing a material dispersed with ultraviolet shielding fine particles according to claim 1, wherein said ultraviolet shielding fine particles have an average particles size of dispersed particles of from 0.01 to 5.0 µm.

3. The method for producing a material dispersed with ultraviolet shielding fine particles according to claim 1, wherein said ultraviolet shielding fine particles are contained in an amount of from 0.1 to 40% by weight.

4. The method for producing a material dispersed with ultraviolet shielding fine particles according to claim 1, wherein said particles comprising inorganic substances having shielding abilities against ultraviolet light are one or more members selected from the group consisting of $TiO_2$, ZnO, $CeO_2$, $BaTiO_3$, $CaTiO_3$, $SrTiO_3$, and SiC.

5. The method for producing a material dispersed with ultraviolet shielding fine particles according to claim 1, wherein said particles comprising inorganic substances having shielding abilities against ultraviolet light comprise $TiO_2$ particles and ZnO particles.

6. The method for producing a material dispersed with ultraviolet shielding fine particles according to claim 1, wherein said silicone dispersant is one or more silicone compounds selected from the group consisting of oxazoline-modified silicones, amino-modified silicones, and polyether-modified silicones.

7. Ultraviolet shielding fine particles or a material dispersed therewith, produced by the method of claim 1.

8. A method of producing a powdery product of ultraviolet shielding fine particles, comprising drying the material dispersed with ultraviolet shielding fine particles produced by the method of claim 1.

9. A powdery product of ultraviolet shielding fine particles produced by the method of claim 8.

10. Cosmetics comprising the material dispersed with ultraviolet shielding fine particles of claim 7.

11. Cosmetics comprising the powdery product of ultraviolet shielding fine particles of claim 9.

12. The method for producing a material dispersed with ultraviolet shielding fine particles according to claim 1, wherein the ultraviolet shielding fine particles are dispersed in silicone oil by a mill treatment.

13. The method for producing a material dispersed with ultraviolet shielding fine particles according to claim 1, wherein the reactive silicone is selected from the group consisting of amino-polyether-modified silicones, carboxyl-modified silicones, carboxyl-polyether-modified silicones, carbinol-modified silicones, mercapto-modified silicones, phenol-modified silicones, vinyl-modified silicones, hydroxy-modified silicones.

14. A method for producing a material dispersed with ultraviolet shielding fine particles, comprising subjecting a starting material liquid mixture comprising particles comprising one or more inorganic substances having shielding abilities against ultraviolet light, one or more reactive silicone dispersants and optionally modified silicones, and a silicone oil to a mill treatment and/or a high-pressure dispersion treatment to disperse the ultraviolet shielding fine particles in the silicone oil, wherein a polar solvent having good compatibility with said silicone oil is further added in at least one step selected from the group consisting of,
(a) process for the preparation of the starting material liquid mixture;
(b) during the mill treatment or high-pressure dispersion treatment; and
(c) after the mill treatment or high-pressure dispersion treatment.

15. The method for producing a material dispersed with ultraviolet shielding fine particles according to claim 1, wherein when the ultraviolet shielding fine particles are coated with a oxide or hydrate, the oxide or hydrate is of an element selected from the group consisting of Al, Si, Zr, Mg, Zn, Ce and Ti.

16. The method for producing a material dispersed with ultraviolet shielding fine particles according to claim 14, wherein when the ultraviolet shielding fine particles are coated with a oxide or hydrate, the oxide or hydrate is of an element selected from the group consisting of Al, Si, Zr, Mg, Zn, Ce and Ti.

17. The method for producing a material dispersed with ultraviolet shielding fine particles according to claim 14, wherein said ultraviolet shielding fine particles have substantially no catalytic activity.

* * * * *